United States Patent [19]

Lee et al.

[11] Patent Number: 4,677,071

[45] Date of Patent: Jun. 30, 1987

[54] ANTIBIOTIC AGENTS FROM *S. COERULEORUBIDUS, RUBIDUS*

[75] Inventors: May D. Lee, Monsey; John H. Martin, New City; Donald B. Borders, Suffern, all of N.Y.; Raymond C. Yao, Carmel, Ind.; Raymond T. Testa, Cedar Grove, N.J.

[73] Assignee: American Cyanamid Company, Stamford, Conn.

[21] Appl. No.: 638,189

[22] Filed: Aug. 6, 1984

Related U.S. Application Data

[62] Division of Ser. No. 362,002, Mar. 25, 1982, Pat. No. 4,499,075.

[51] Int. Cl.$^4$ .................. C12N 1/20; C12P 21/00; C12R 1/465

[52] U.S. Cl. .................. 435/253; 435/68; 435/886

[58] Field of Search .................. 435/253, 68, 886

*Primary Examiner*—Thomas G. Wiseman
*Assistant Examiner*—Jayme A. Huleatt
*Attorney, Agent, or Firm*—H. G. Jackson

[57] ABSTRACT

This invention relates to new polypeptide antibiotics designated LL-BO2964α, LL-BO2964β, LL-BO2964γ, and a mixture thereof designated LL-BO2964, produced during microbiological fermentation, under controlled conditions, using a new strain of *Streptomyces coeruleorubidus* subspecies *rubidus* or a mutant thereof. The new antibiotics are active against a variety of microorganisms and are also useful in treating tuberculosis.

4 Claims, 15 Drawing Figures

ANTIBIOTIC AGENTS FROM S. COERULEORUBIDUS, RUBIDUS

This is a divisional application of copending application Ser. No. 362,002, filed Mar. 25, 1982 U.S. Pat. No. 4,499,075, issued Feb. 12, 1985.

BACKGROUND OF THE INVENTION

This invention relates to new antibiotics designated LL-BO2964α, LL-BO2964β, LL-BO2964γ and LL-BO2964, and to their production by fermentation.

This invention also relates to a new strain of *Streptomyces coeruleorubidus* subspecies *rubidus* and mutants thereof which produce polypeptide antibiotics.

The new antibiotics of the invention appear to be similar to the family of polypeptide compounds such as antibiotic 6798RP disclosed in British Pat. No. 846,801; antibiotic FR3383 disclosed in unexamined Japanese patent application Nos. 1054-988 (Derwent Abstract No. 49101X) and 2093-701 (Derwent Abstract No. 66033Y) and Japan Kokai No. 77-93,701; and the A-38533 antibiotics disclosed in U.S. Pat. No. 4,180,564 and in "A-38533, A New Antipseudomonal Antibiotic: Fermentation, Isolation, and Structure Studies", *Current Chemotherapy and Infectious Disease,* Abs. No. 1032, 19th Interscience Conf., October 1979. The antibiotics of the present invention, however, show distinguishing physical characteristics over these polypeptide compounds, including but not limited to differences in elemental analysis, UV spectrum, and high pressure liquid chromatographic retention times.

SUMMARY OF THE INVENTION

The new antibiotics of the invention are arbitrarily designated LL-BO2964α, LL-BO2964β, and LL-BO2964γ The designation LL-BO2964 indicates a mixture in any proportion of two or more of the α, β, and γ components and this designation with the identities of the included components will be used herein whenever a mixture of the components is discussed.

The antibiotics are present as an associated mixture when produced by a microbial culture fermentation. The ratios of components in the associated mixture will vary depending on the fermentation conditions and the culture strain used. Typically, the antibiotics are formed by cultivation of a new strain of *Streptomyces coeruleorubidus* subspecies *rubidus* or by cultivation of a mutant thereof, having accession numbers NRRL 12372 and NRRL 12373 respectively.

The antibiotics LL-BO2964α, β, and γ are solid, optically active, amphoteric polypeptides having the characteristic, significant carbon-13 nuclear magnetic resonance absorptions presented in Table I, infra. These absorptions uniquely characterize each antibiotic and differentiate them from other polypeptide antibiotics. The antibiotics of the invention also exhibit the ultraviolet, visible, infrared, proton and carbon-13 nuclear magnetic resonance spectra depicted in FIGS. 1 through 15. The elemental analyses for the α, β, and γ antibiotics of the invention show the presence of carbon, hydrogen and nitrogen but no sulfur. Based upon hydrolysis data, the antibiotics of the invention at least contain one residue each of uracil, glycine, alanine, beta-alanine, 2-amino-3-N-methylaminobutyric acid, and m-tyrosine.

The pharmacologically acceptable acid addition salts of the amphoteric polypeptide antibiotics are also included within the invention. The acids forming such salts are those pharmacologically acceptable organic and inorganic acid reagents which will at least in part complex the polypeptide antibiotics of the invention but will not destroy them.

The antibiotics of the invention show in vitro and in vivo antibacterial activity as well as antitubercular activity.

BRIEF DESCRIPTION OF THE DRAWINGS

The drawings depict the ultraviolet (UV), visible (Vis), infrared (IR) and nuclear magnetic resonance (proton or $^1$HNMR, and carbon-13 or $^{13}$CNMR) spectra of the new antibiotics LL-BO2964α, LL-BO2964β, and LL-BO2964γ in their substantially pure forms. Chart A correlates FIGS. 1 through 15 with these individual antibiotics.

CHART A
UV-VIS, IR, $^1$HNMR AND $^{13}$CNMR Spectra of Individual Antibiotics

Figure 1:
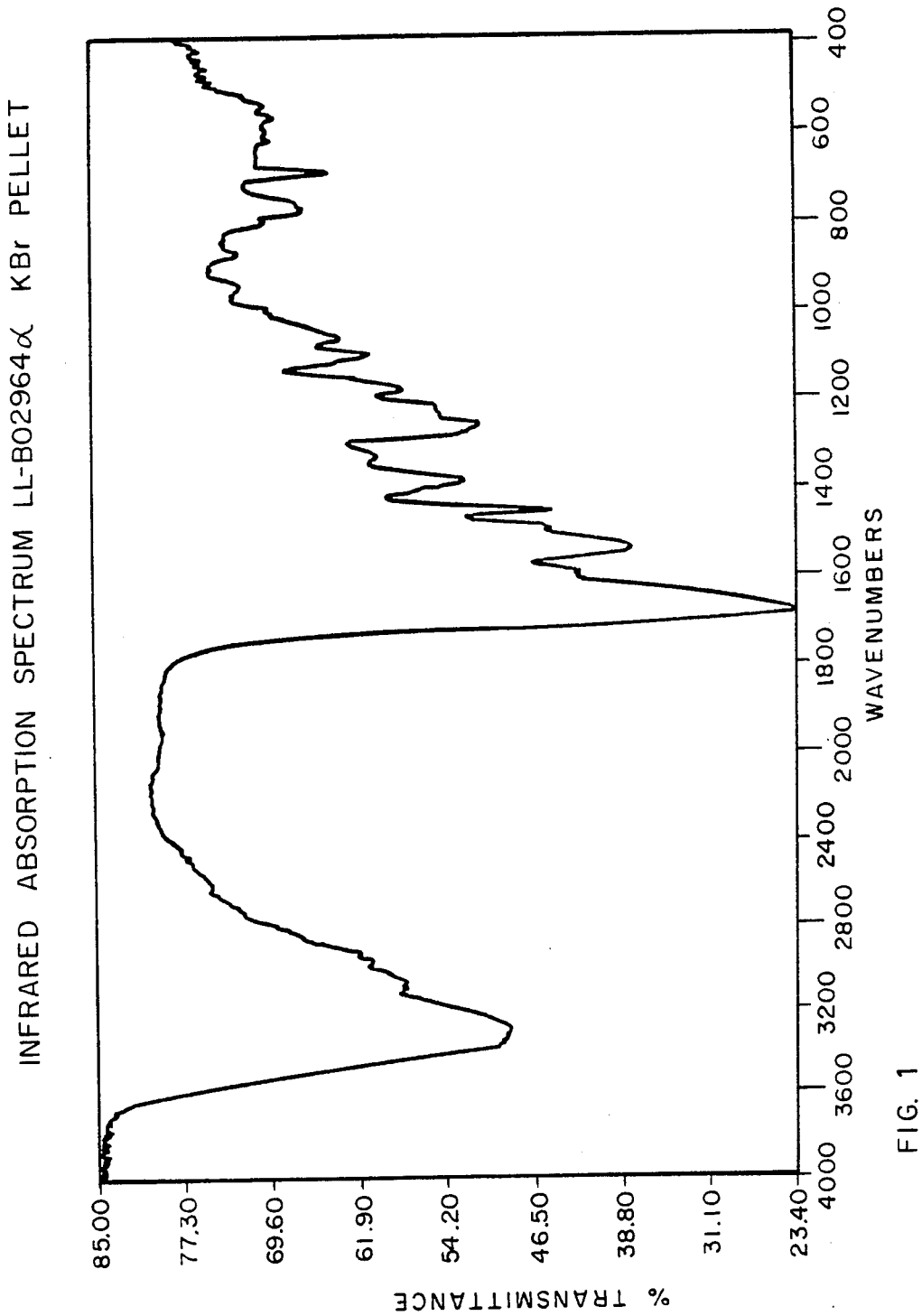
Figure 2:
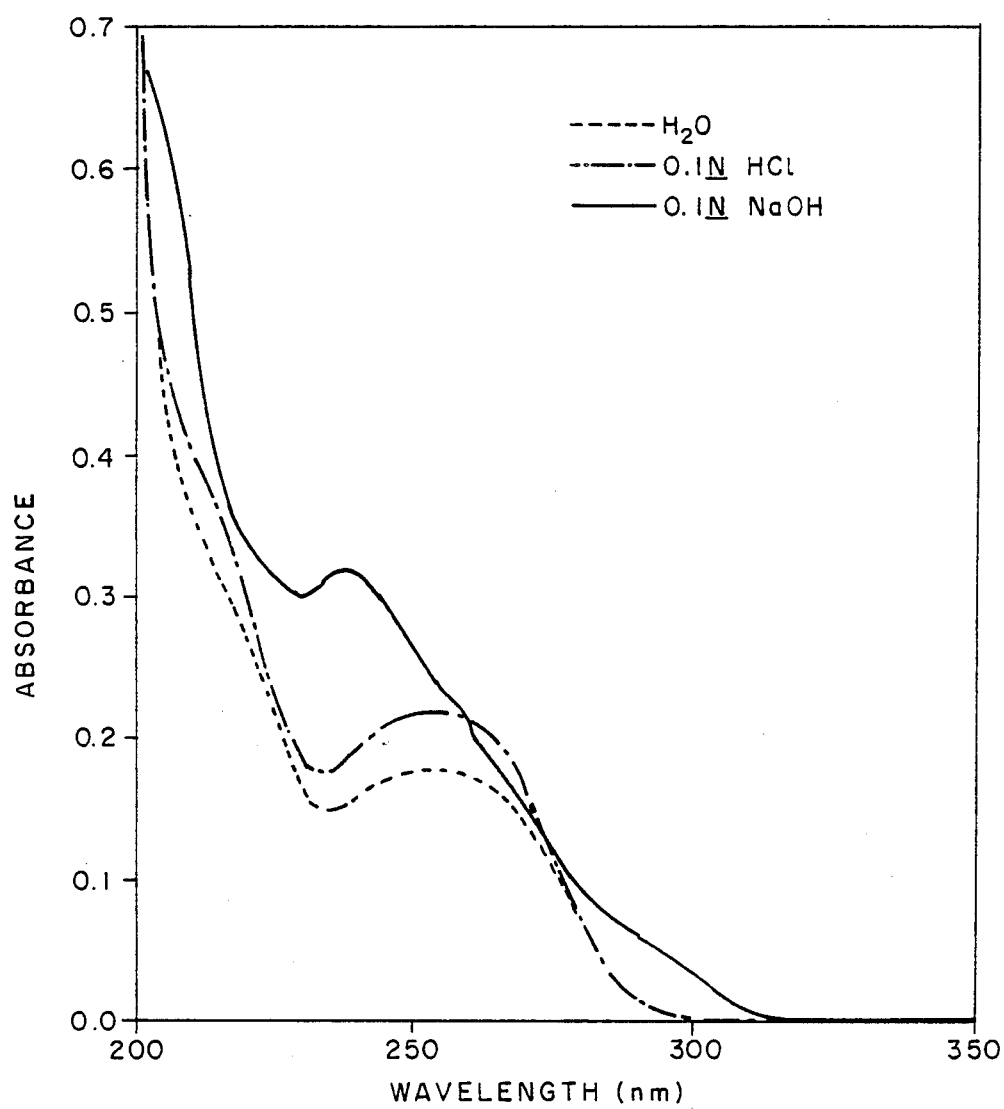
Figure 3:
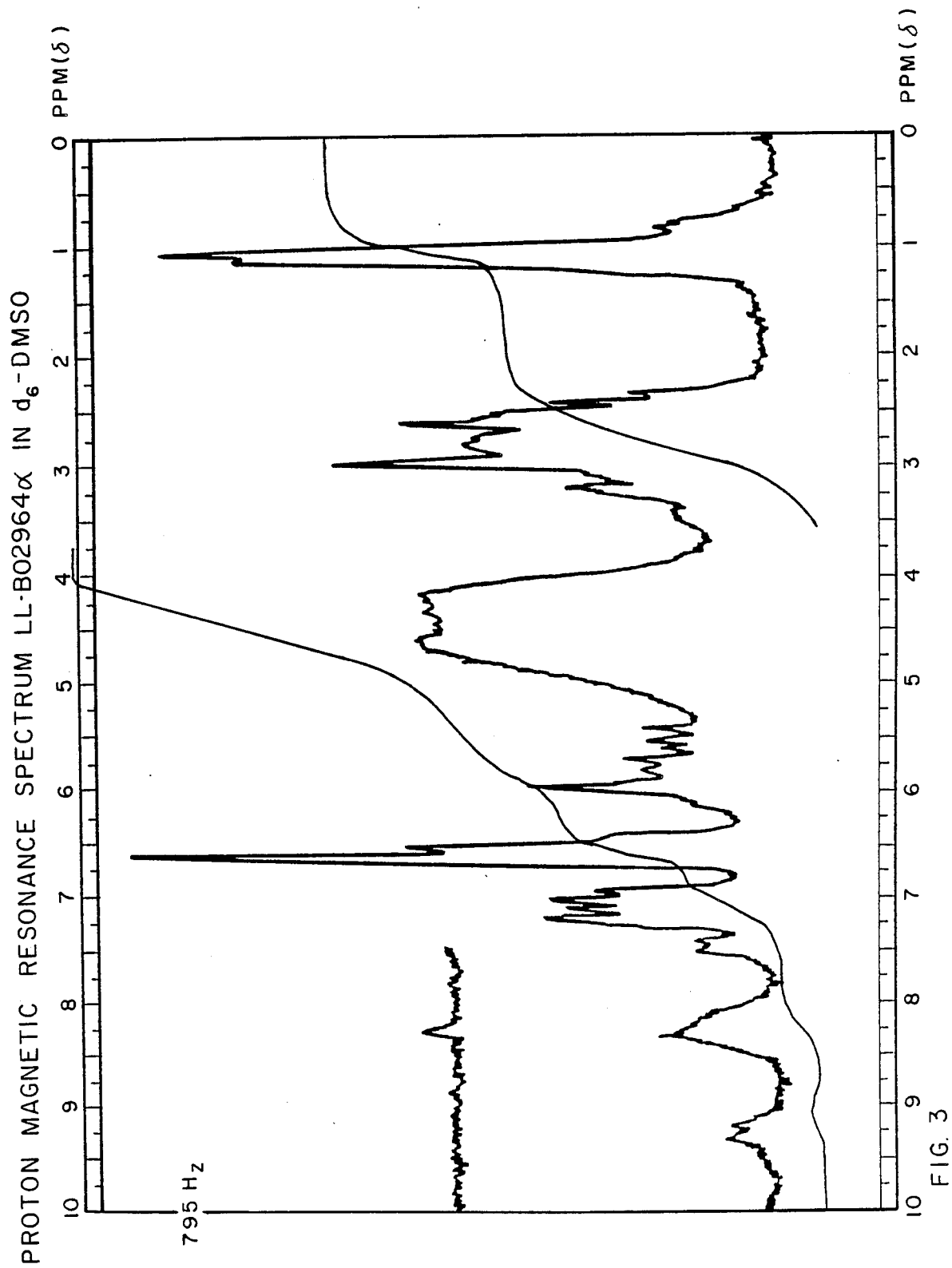
Figure 4:
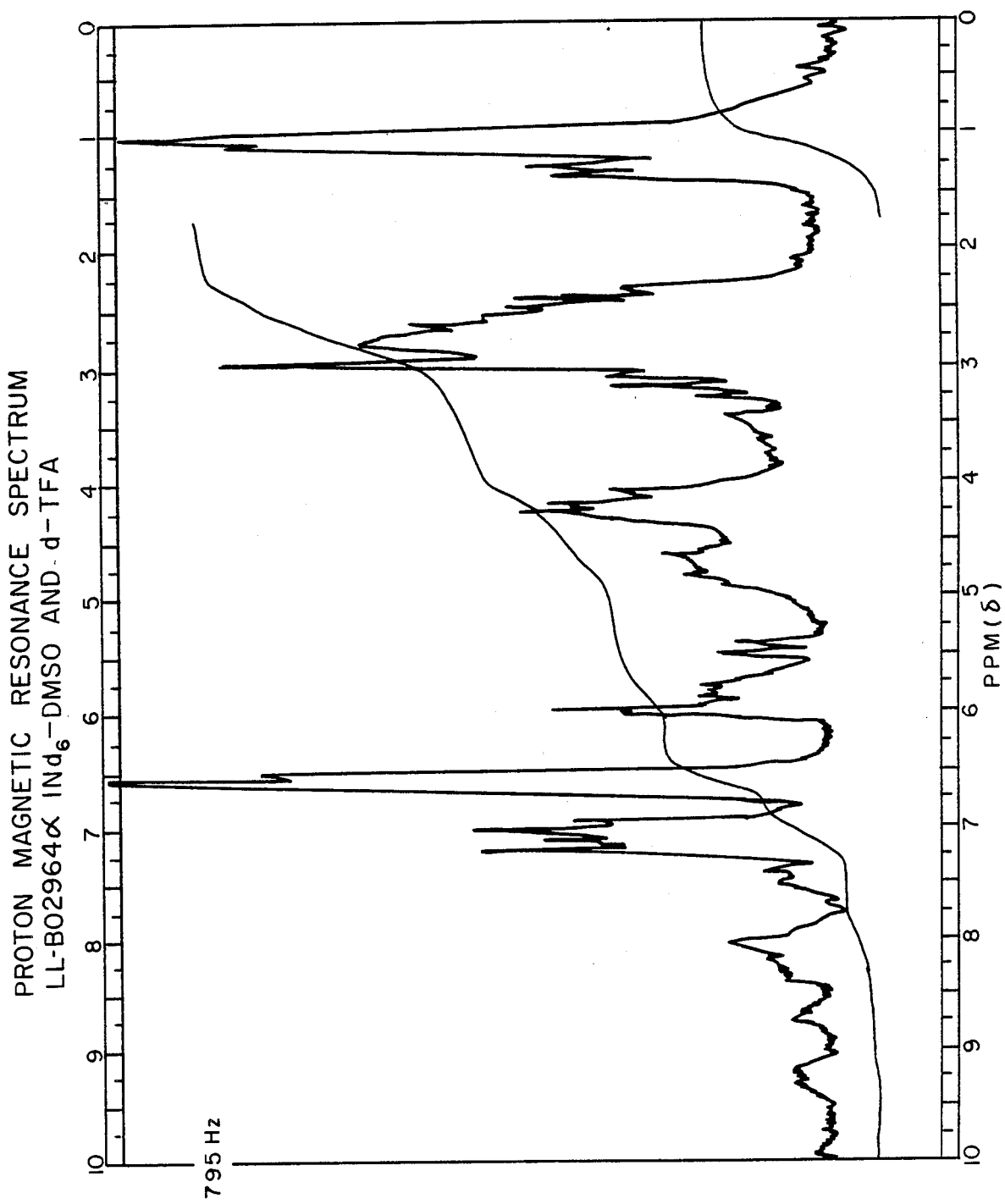
Figure 5:
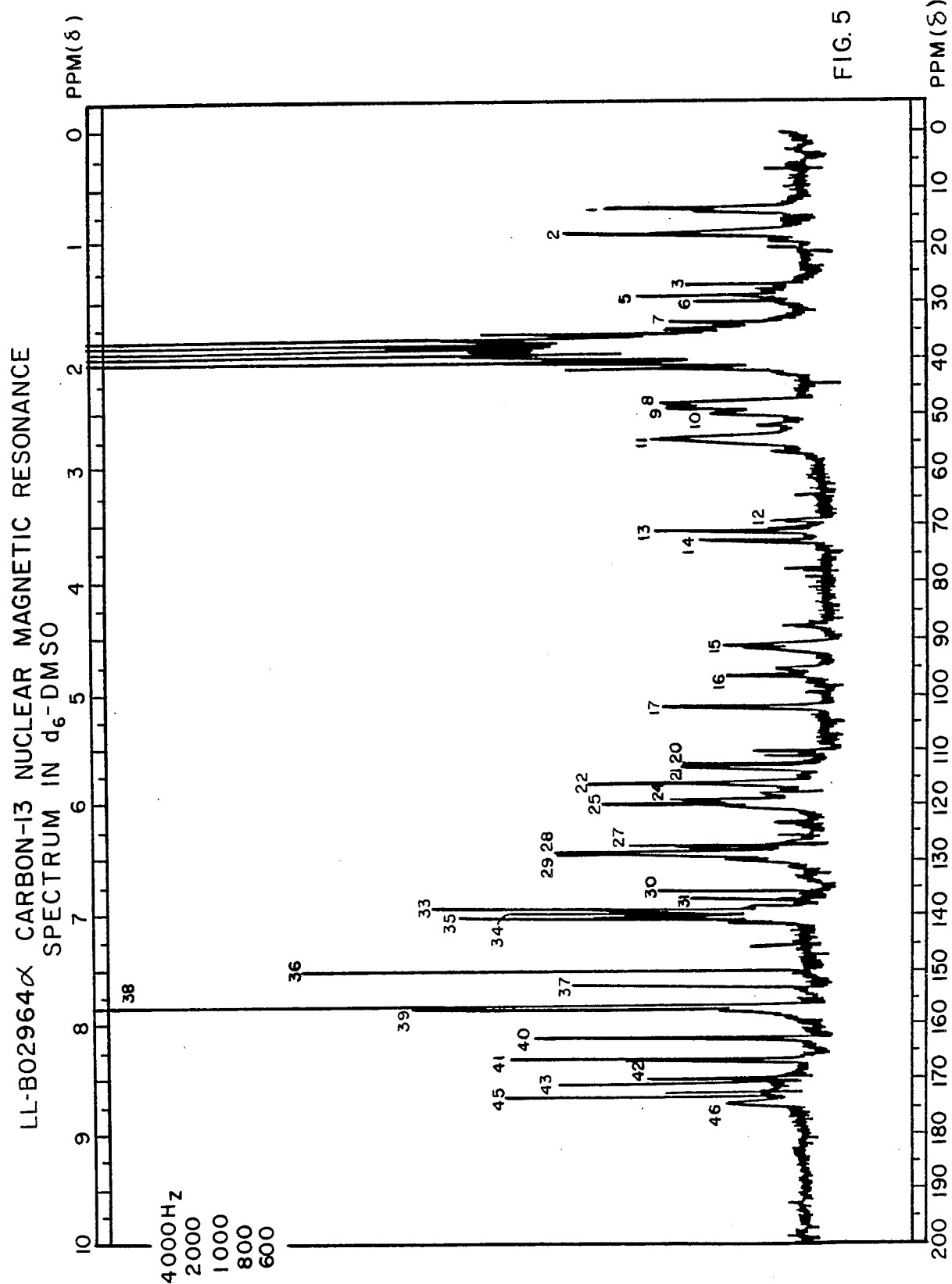
Figure 6:
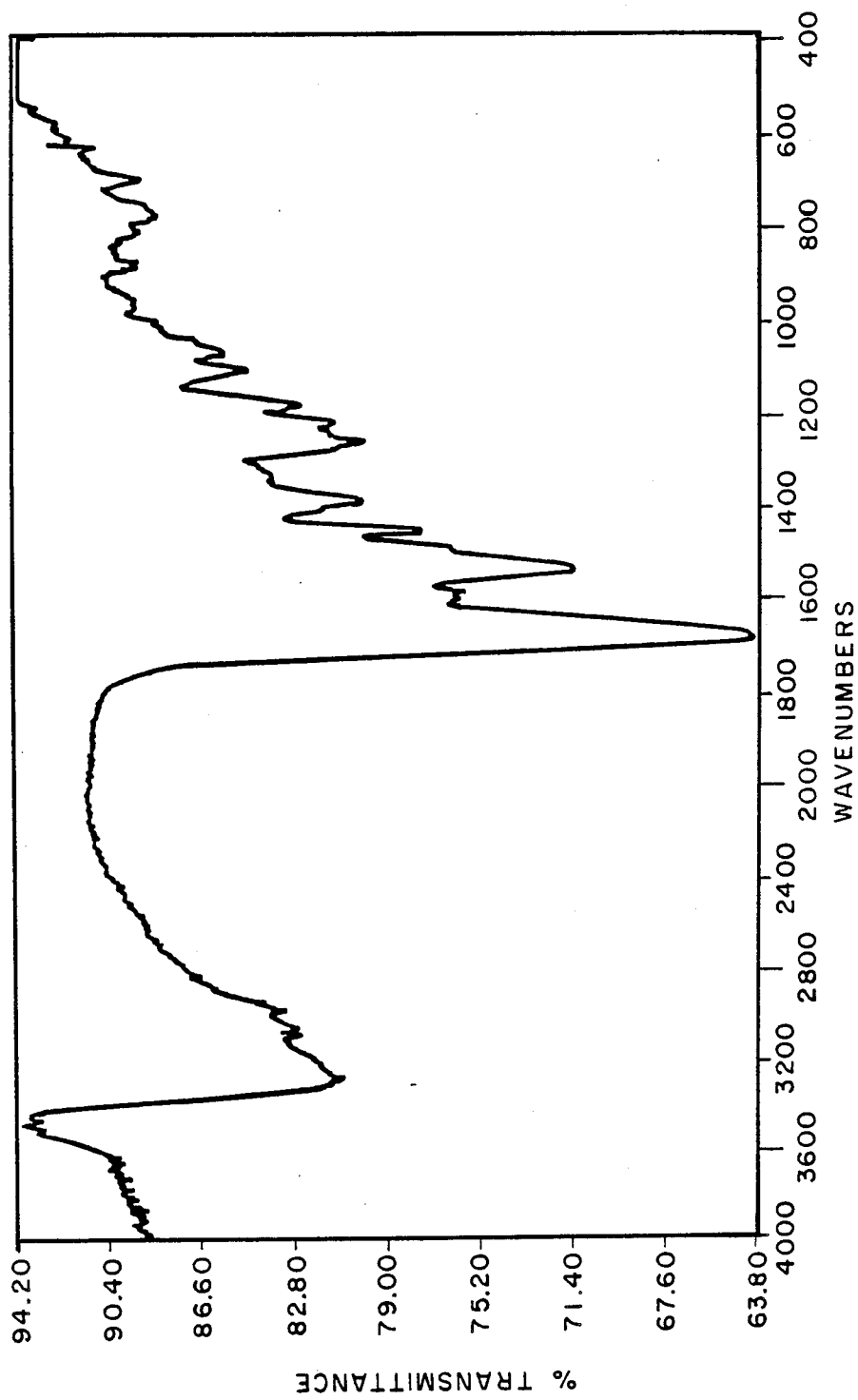
Figure 7:
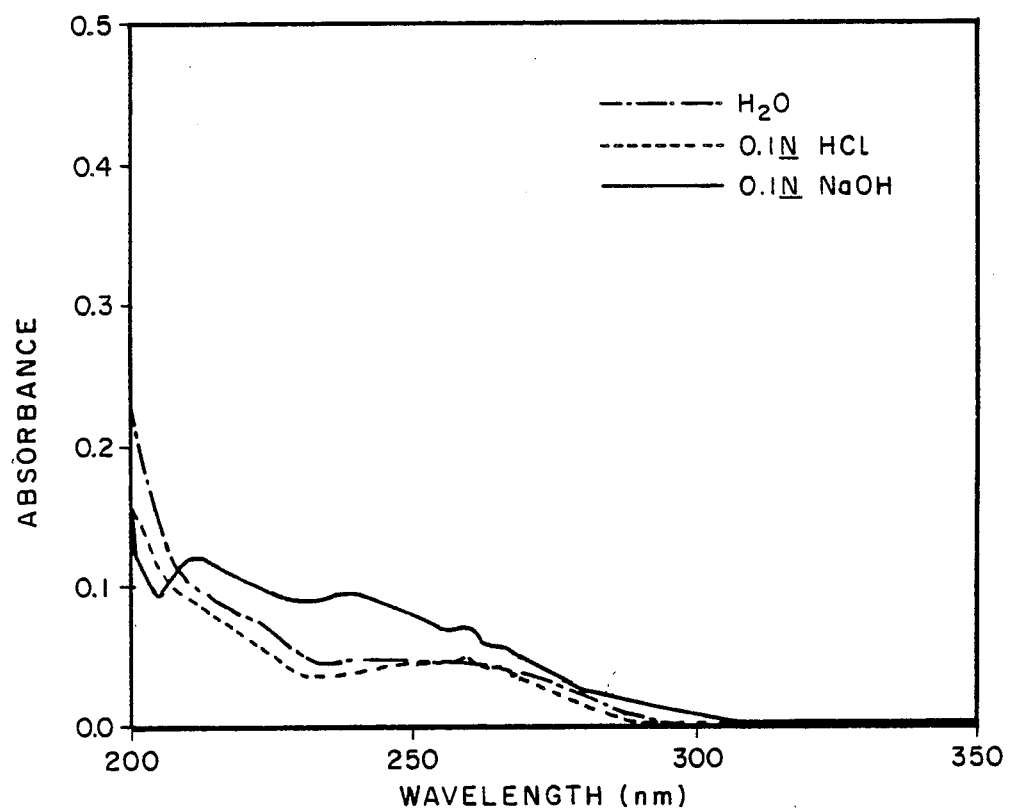
Figure 8:
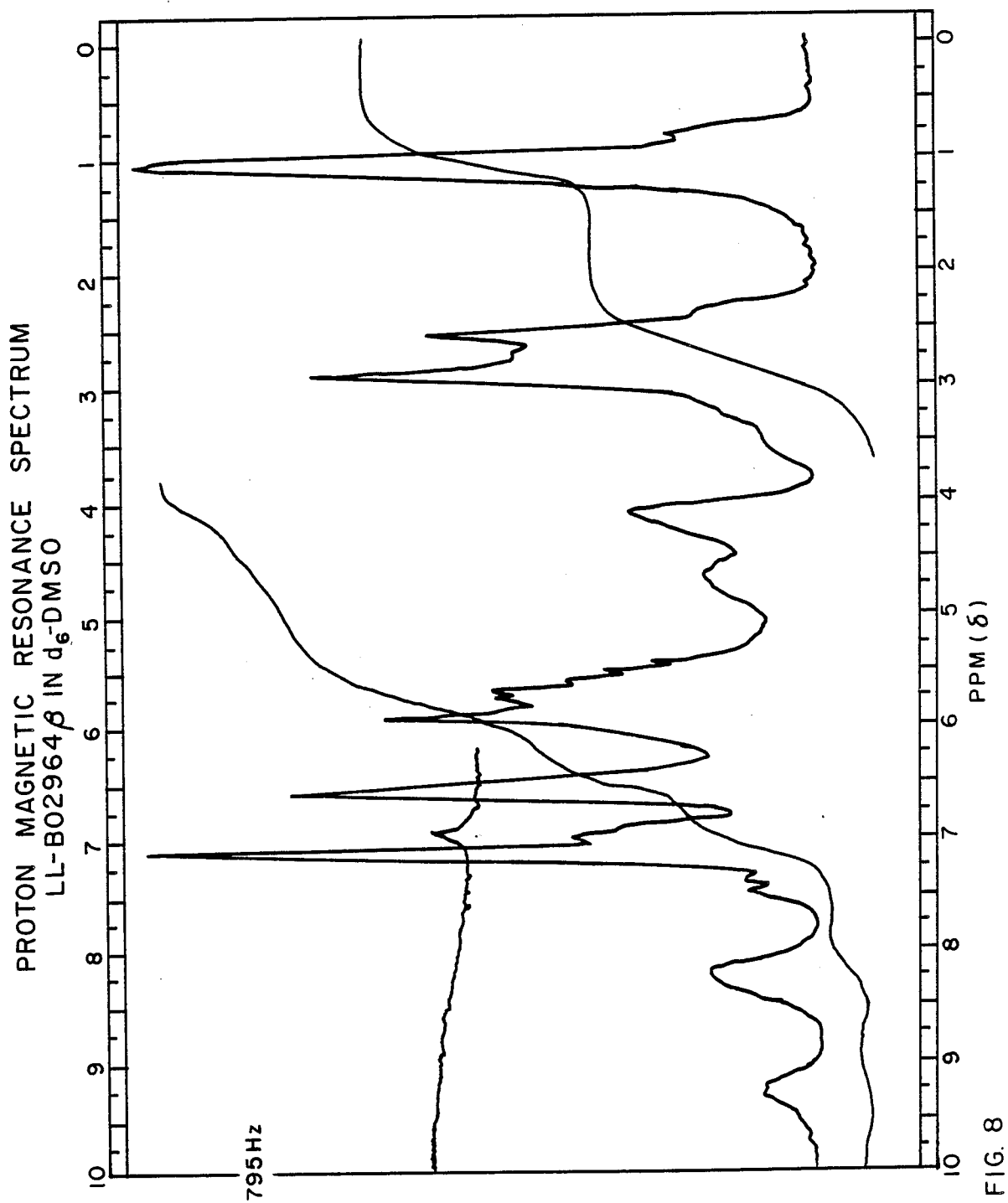
Figure 9:
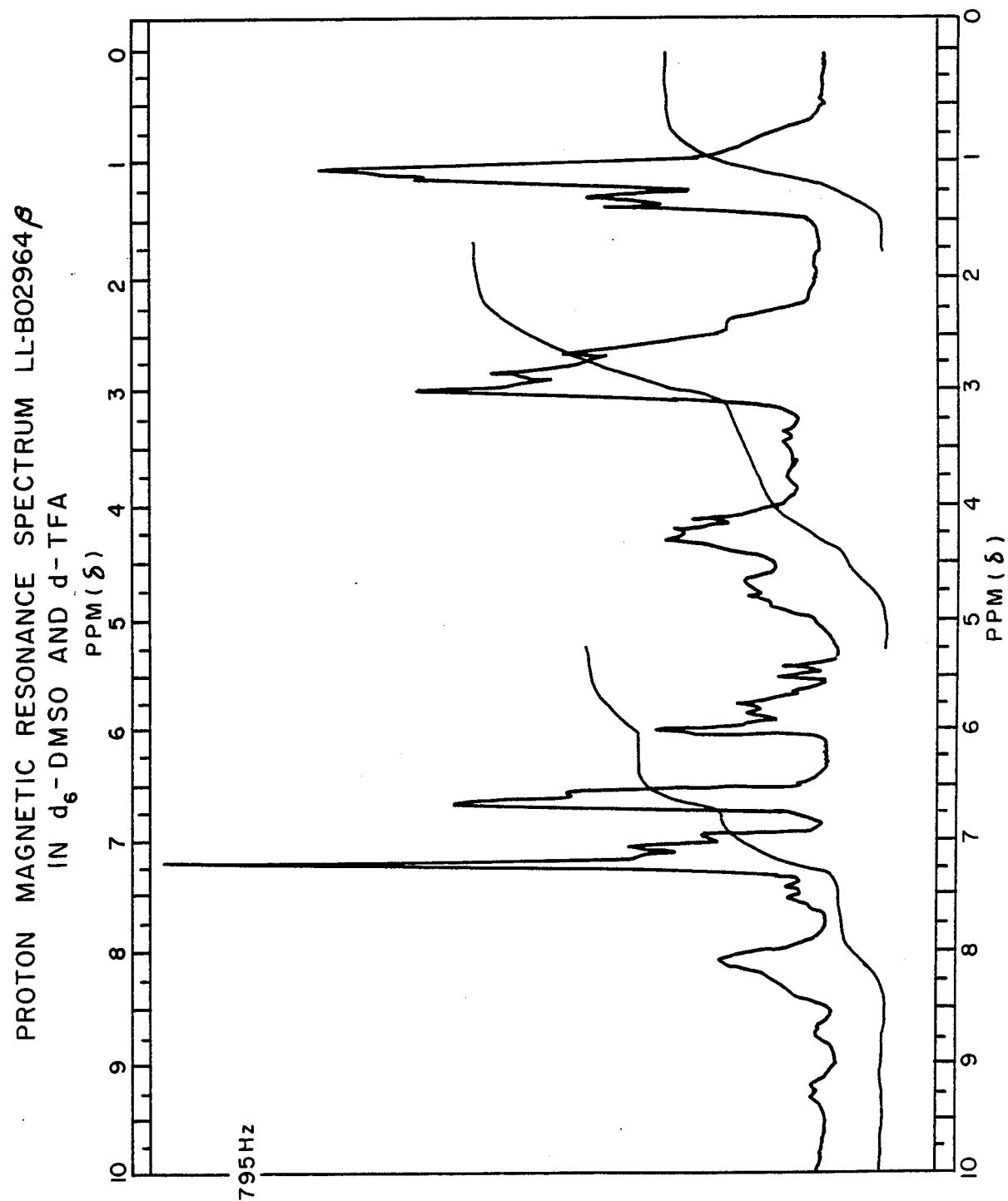
Figure 10:
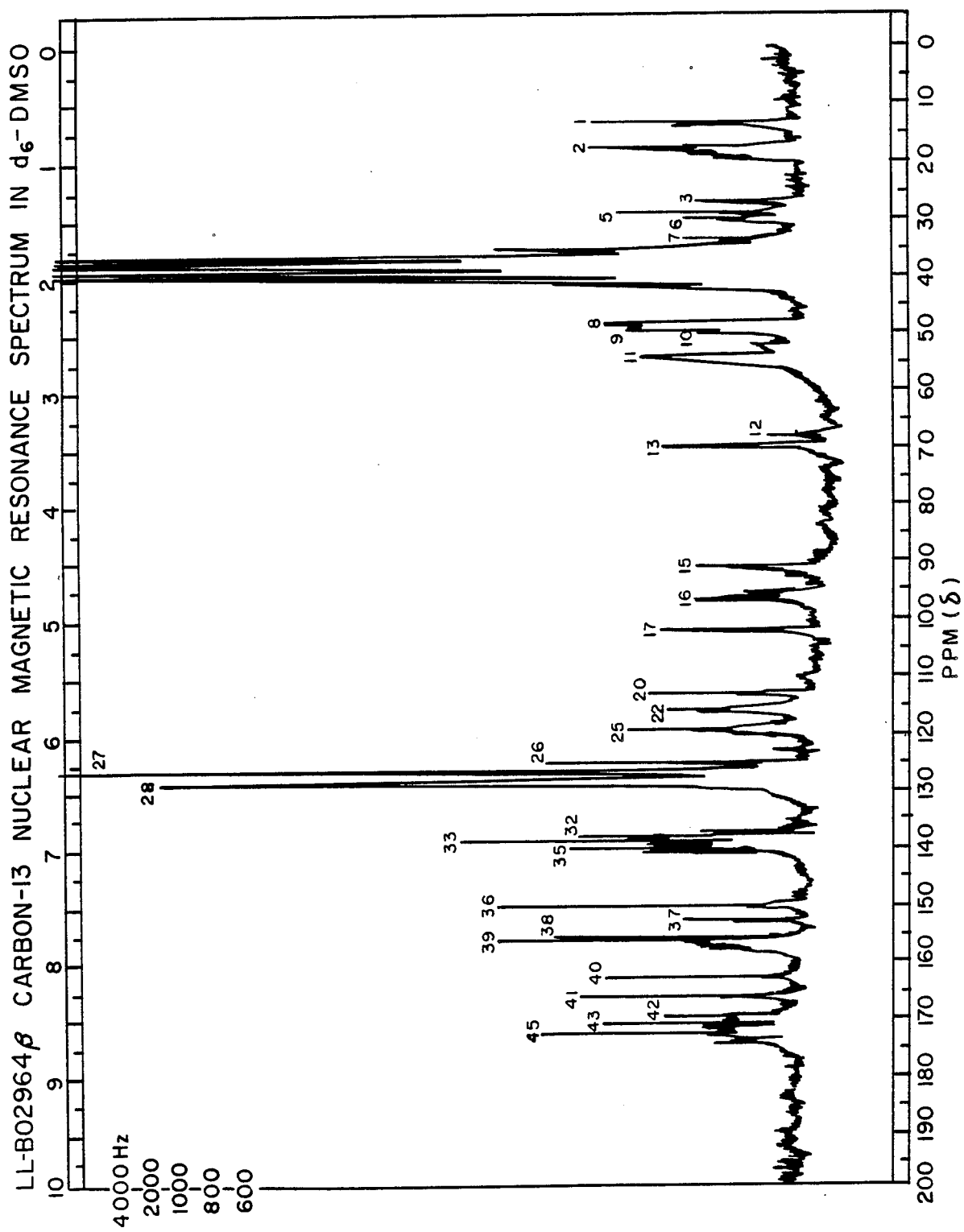
Figure 11:
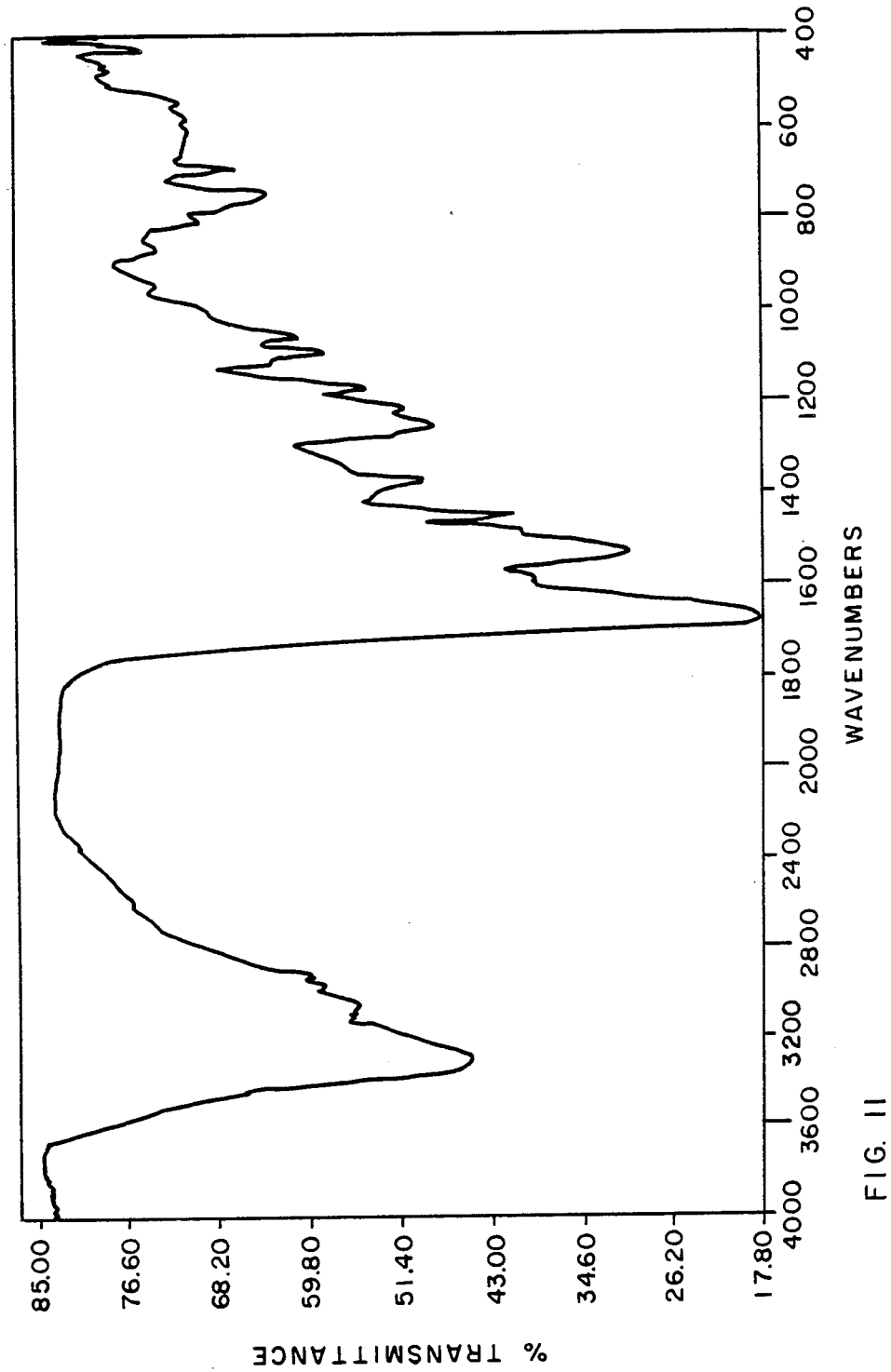
Figure 12:
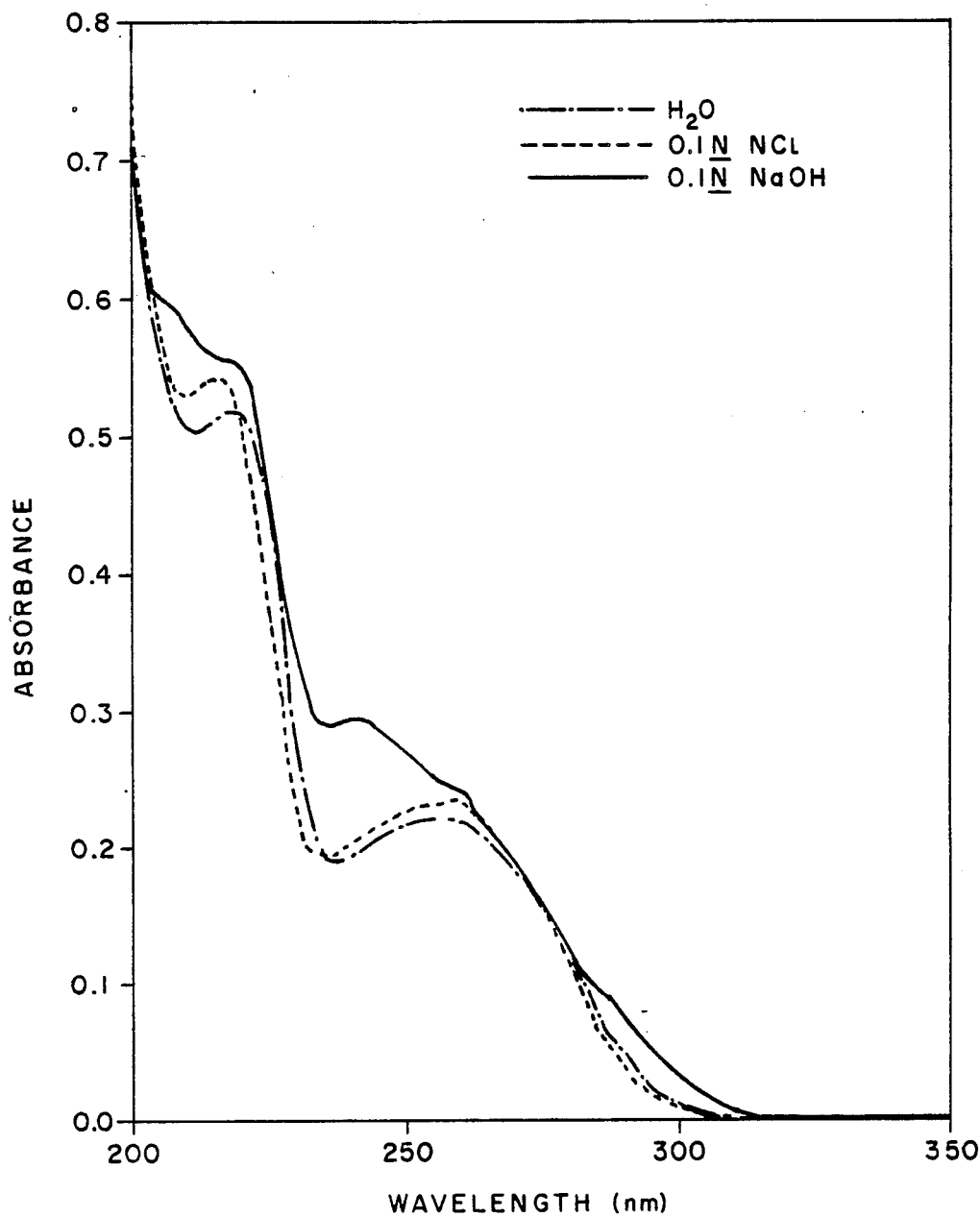
Figure 13:
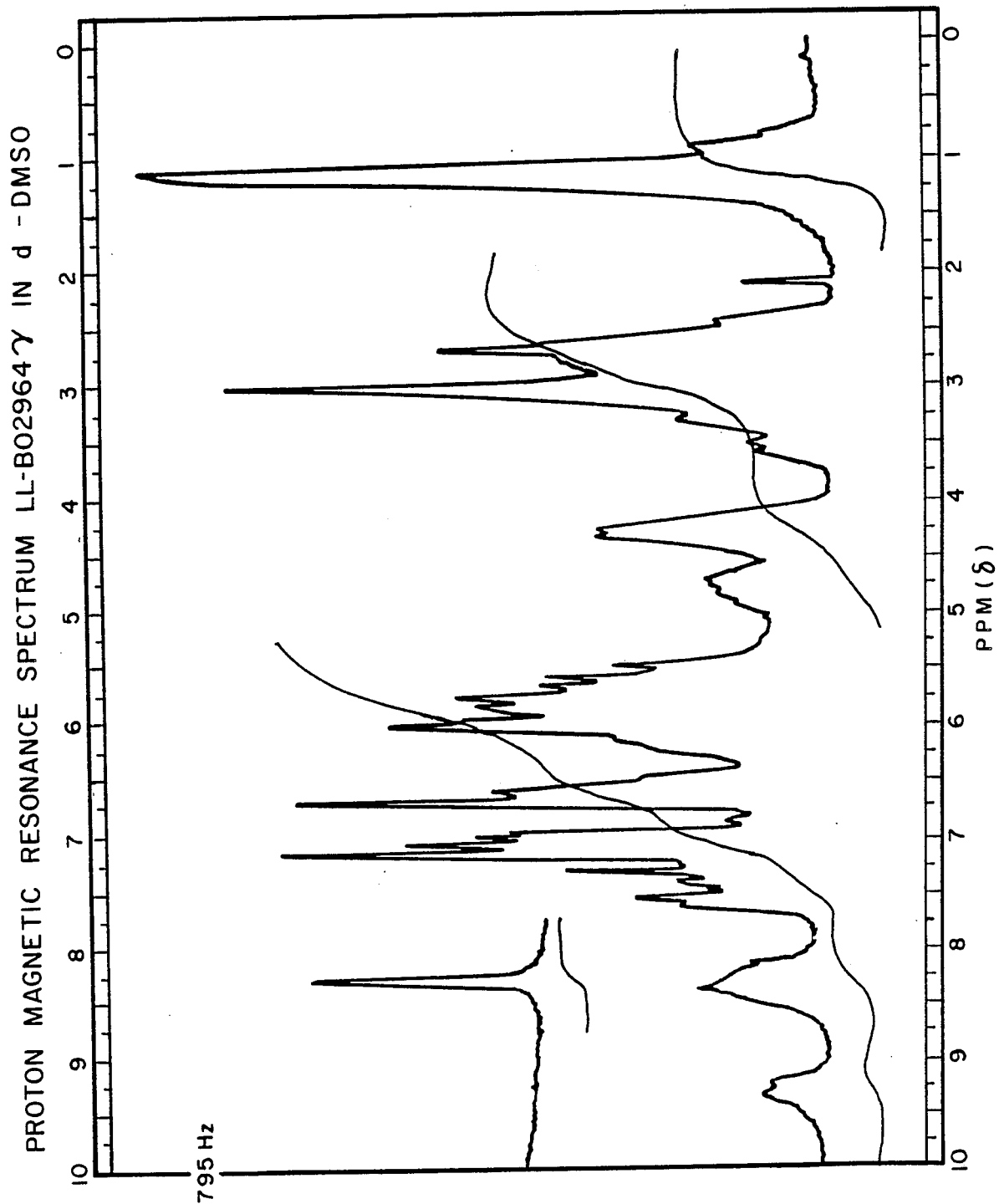
Figure 14:
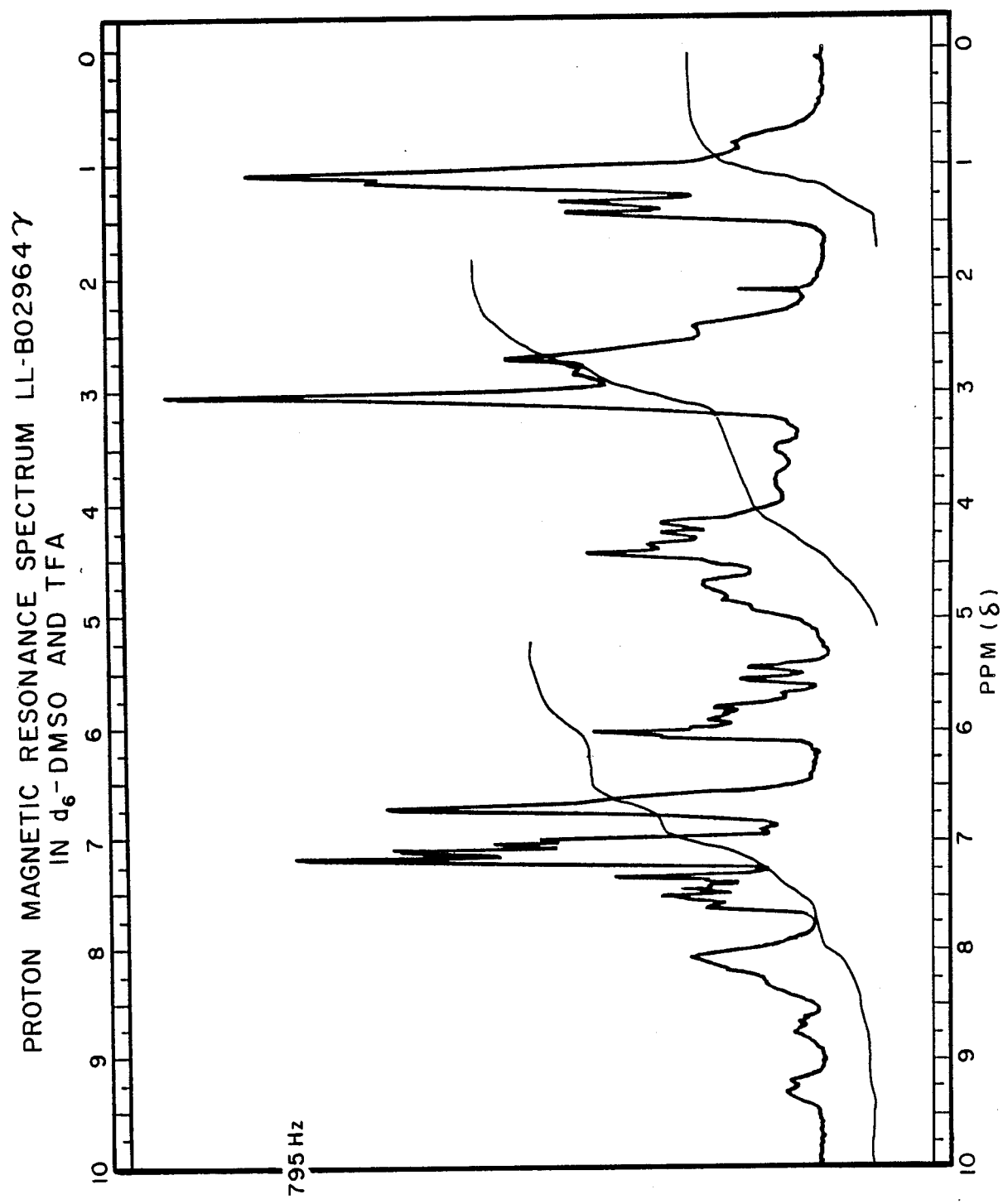
Figure 15:
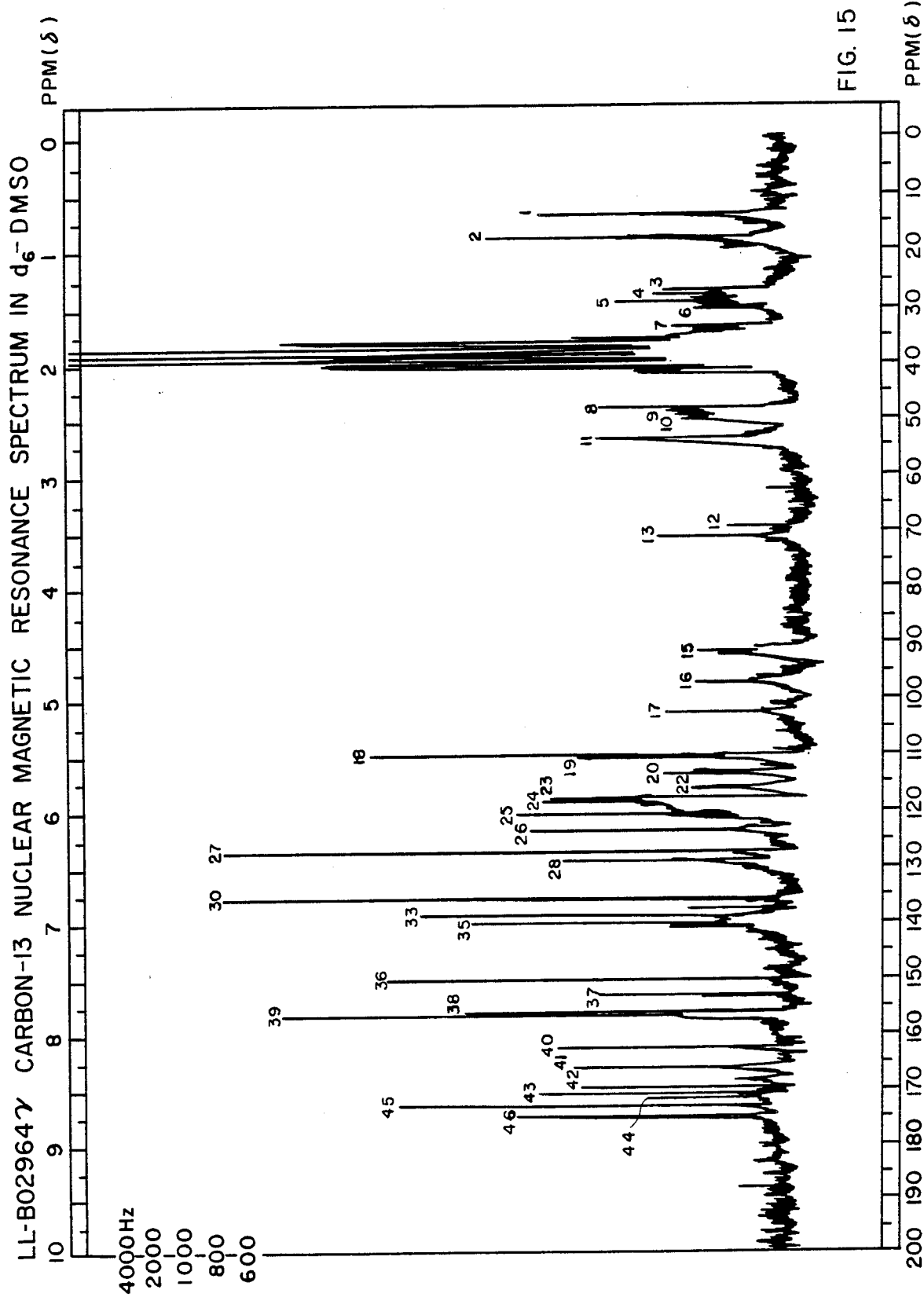

| Antibiotic | UV-VIS (water) | IR(KBr) | $^1$HNMR (DMSO-$d_6$) | $^{13}$CNMR (DMSO-$d_6$) |
|---|---|---|---|---|
| LL-BO2964α | FIG. 2 | FIG. 1 | FIGS. 3, 4 | FIG. 5 |
| LL-BO2964β | FIG. 7 | FIG. 6 | FIGS. 8, 9 | FIG. 10 |
| LL-BO2964γ | FIG. 12 | FIG. 11 | FIGS. 13, 14 | FIG. 15 |

DETAILED DESCRIPTION OF THE INVENTION

The new antibiotics LL-BO2964α, LL-BO2964β, and LL-BO2964γ are closely related polypeptides produced by fermentation of a new strain of *Streptomyces coeruleorubidus* subspecies *rubidus* and a mutant thereof. They are recovered from the fermentation broth as a mixture and the ratio of the individual components in the mixture varies depending on the fermentation conditions. In general, LL-BO9264γ will be the major component found in the antibiotic mixture typically produced. Isolation of the component mixture LL-BO2964 from fermented culture followed by chromatographic or other known method of separation produces grossly separated component fractions. The fractions can be further purified by known methods to produce substantially pure primary components LL-BO2964α, β, and γ. Although the grossly separated component fractions each overwhelmingly constitute one primary component, the γ component fraction in this somewhat impure state appears to contain two additional subcomponents. These subcomponents are believed to be bound in complex form with the primary component, LL-BO2964γ, and are also polypeptide antibiotics. They are present in minor amounts and have a composition and structure which appears to be very close to that of the primary component LL-BO2964γ. The α and β component fraction, in this somewhat impure state also appear to be complexed with minor amounts of structurally similar polypeptide subcomponents. In general, however, the primary components, LL-BO2964α, β, and γ will be present in an overwhelmingly high proportion relative to the subcomponents when the antibiotic mixture is grossly separated.

The novel antibiotics of the present invention are amphoteric peptides and thus are capable of forming acid-addition salts with a variety of pharmacologically acceptable organic and inorganic salt forming reagents. Such salts may be prepared from the appropriate form of the antibiotic and one or more equivalents of an acid such as sulfuric, phosphoric, hydrochloric, hydrobromic, sulfamic, citric, maleic, fumaric, tartaric, acetic, benzoic, gluconic, ascorbic and the like. The pharmacologically acceptable acid-addition salts would be expected to be solids, as is typical of amphoteric polypeptides in general. It follows that they would be relatively soluble in water, methanol and ethanol but would be relatively insoluble in non-polar organic solvents such as diethyl ether, chloroform, benzene, toluene and the like.

Spectroscopic characteristics provided by $^{13}$CNMR data will generally serve to identify an organic compound being examined. The information provided will be characteristic of that organic compound alone. Moreover, the frequencies of the individual absorptions of the $^{13}$CNMR can be measured with high precision and will not be affected by the concentration of the organic compound being examined. Therefore, each set of significant carbon-13 nuclear magnetic resonance absorptions (Abs) produced by each of the antibiotics of the invention uniquely characterizes each and differentiates it from other polypeptide antibiotics. These sets of significant $^{13}$CNMR absorptions for LL-BO2964α, β, and γ are given in Table I. The absorption (Abs) values are in parts per million in dimethyl sulfoxide-$d_6$(DMSO-$d_6$) relative to tetramethyl silane (TMS). The Peak Nos. correspond to the numbered peaks of the $^{13}$CNMR spectra.

TABLE I

Sets Of Significant $^{13}$CNMR Absorptions (Abs) For The Primary Components LL-BO2964α, β and γ

| Peak No. | Abs | Peak No. | Abs | Peak No. | Abs |
|---|---|---|---|---|---|
| α Primary Component LL-BO2964α ||||||
| 1 | 13.9 | 16 | 96.7 | 31 | 137.3 |
| 2 | 18.4 | 17 | 102.1 | 32 | |
| 3 | 27.3 | 18 | | 33 | 138.9 |
| 4 | | 19 | | 34 | 139.6 |
| 5 | 29.3 | 20 | 112.9 | 35 | 140.4 |
| 6 | 30.5 | 21 | 113.4 | 36 | 150.3 |
| 7 | 33.9 | 22 | 116.2 | 37 | 152.9 |
| 8 | 48.5 | 23 | | 38 | 156.9 |
| 9 | 49.5 | 24 | 119.3 | 39 | 157.3 |
| 10 | 50.4 | 25 | 119.9 | 40 | 162.7 |
| 11 | 55.0 | 26 | | 41 | 166.4 |
| 12 | 69.9 | 27 | 127.6 | 42 | 170.1 |
| 13 | 71.4 | 28 | 128.6 | 43 | 171.0 |
| 14 | 73.0 | 29 | 129.6 | 44 | |
| 15 | 91.5 | 30 | 135.8 | 45 | 173.1 |
| β Primary Component LL-BO2964β ||||||
| 1 | 13.9 | 16 | 96.7 | 31 | |
| 2 | 18.3 | 17 | 102.1 | 32 | 138.4 |
| 3 | 27.3 | 18 | | 33 | 138.9 |
| 4 | | 19 | | 34 | |
| 5 | 29.3 | 20 | 113.4 | 35 | 140.4 |
| 6 | 30.4 | 21 | | 36 | 150.3 |
| 7 | 33.9 | 22 | 115.7 | 37 | 152.9 |
| 8 | 48.9 | 23 | | 38 | 156.9 |
| 9 | 49.6 | 24 | | 39 | 157.3 |
| 10 | 50.4 | 25 | 119.4 | 40 | 162.7 |
| 11 | 54.9 | 26 | 125.7 | 41 | 166.4 |
| 12 | 69.4 | 27 | 127.7 | 42 | 169.9 |
| 13 | 71.3 | 28 | 129.3 | 43 | 171.0 |
| 14 | | 29 | | 44 | |
| 15 | 91.4 | 30 | | 45 | 173.1 |
| γ Primary Component LL-BO2964γ ||||||
| 1 | 13.9 | 16 | 96.7 | 31 | |
| 2 | 18.4 | 17 | 102.2 | 32 | |
| 3 | 27.4 | 18 | 110.3 | 33 | 138.9 |
| 4 | 28.1 | 19 | 111.0 | 34 | |
| 5 | 29.3 | 20 | 113.4 | 35 | 140.4 |
| 6 | 30.4 | 21 | | 36 | 150.3 |
| 7 | 33.9 | 22 | 115.7 | 37 | 153.0 |

TABLE I-continued

Sets Of Significant $^{13}$CNMR Absorptions (Abs) For The Primary Components LL-BO2964α, β and γ

| Peak No. | Abs | Peak No. | Abs | Peak No. | Abs |
|---|---|---|---|---|---|
| 8 | 48.7 | 23 | 118.0 | 38 | 156.9 |
| 9 | 49.4 | 24 | 118.5 | 39 | 157.4 |
| 10 | 50.4 | 25 | 120.5 | 40 | 162.7 |
| 11 | 54.2 | 26 | 123.4 | 41 | 166.4 |
| 12 | 69.5 | 27 | 127.6 | 42 | 170.0 |
| 13 | 71.4 | 28 | 129.0 | 43 | 171.1 |
| 14 | | 29 | | 44 | 171.9 |
| 15 | 91.5 | 30 | 135.8 | 45 | 173.1 |
| | | | | 46 | 174.9 |

The antibiotic components α, β and γ are isolated as noncrystalline, white fluffy powders. Their approximate elemental compositions are shown in Table II.

TABLE II

Elemental Analysis of LL-BO2964 Components

| Component | % Carbon | % Hydrogen | % Nitrogen | % Sulfur |
|---|---|---|---|---|
| LL-BO2964α | 50.9 | 5.7 | 14.4 | 0 |
| LL-BO2964β | 50.9 | 5.8 | 13.6 | 0 |
| LL-BO2964γ | 52.9 | 5.8 | 15.1 | 0 |

The optical rotation values of the α, β and γ antibiotics are shown in Table III.

TABLE III

Optical Rotation of LL-BO2964 Components

| Components | Optical Rotation |
|---|---|
| LL-BO2964α | $[\alpha]_D^{25} = -10°$ (C = 2.77, water) |
| LL-BO2964β | $[\alpha]_D^{25} = -19 \pm 2°$ (C = 0.5, water) |
| LL-BO2964γ | $[\alpha]_D^{25} = -20 \pm 2°$ (C = 0.5, water) |

The UV-VIS, IR, $^1$HNMR and $^{13}$CNMR spectra of the LL-BO2964 components are presented in FIGS. 1 through 15 and are correlated in foregoing Chart A. The numbered peaks of the $^{13}$CNMR spectra correspond to the appropriate antibiotic peak numbers listed in Table I.

The nucleotide base and amino acid residues produced by acid degradation of each of the antibiotics of the invention include uracil and the following amino acids.

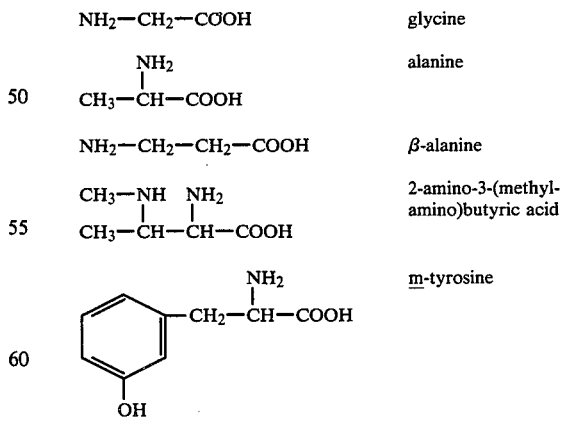

Based on the amounts of each base or amino acid found, the polypeptide chain of each antibiotic of the invention at least contains one residue each of uracil, glycine, alanine, β-alanine, 2-amino-3-(methylamino)butyric acid and m-tyrosine.

In addition to uracil and the foregoing five amino acids, a hydantoin (A), formed from alanine and m-tyrosine, is present in the acid hydrolysate of LL-BO2964α, a hydantoin (B), formed from alanine and phenylalanine is present in the acid hydrolysate of LL-BO2964β and a hydantoin (C), formed from alanine and p-tyrosine, is present in the acid hydrolysate of LL-BO2964γ. The meta and para substitutions of the tyrosines forming the A and C hydantoins are probable but not certain. These hydantoins have the following formulas:

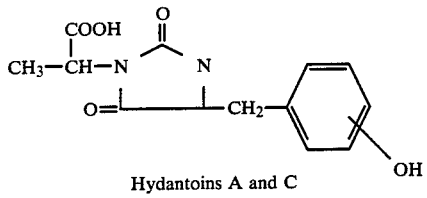

Hydantoins A and C

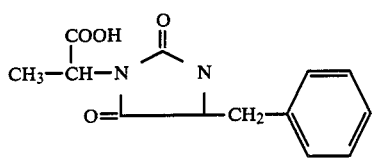

Hydantoin B

Chemical reaction studies of LL-BO2964γ have shown that it contains only one free amino group which can be N--acylated with acetic anhydride in methanol. This group has been identified as the N-methylamino functionality of 2-amino-3-(methylamino)butyric acid. It is believed that the α and β components would provide similar reaction results with acetic anhydride in methanol.

Although these degradation data do not permit elucidation of a molecular structure for any of the α, β and γ antibiotic components, a hypothetical partial molecular structure of each component based on these data is a five unit peptide chain of the foregoing five amino acid residues arranged in an unknown sequence, which may be different for each individual component, wherein each chain may be joined to a uracil moiety at the carboxyl terminus. An intact hydantoin moiety having an identity relating to each individual component as described above may also be present but it is more likely that the amino acids making up the hydantoin moiety are actually present in the molecular structure and the hydantoin is probably formed during hydrolysis. Other moieties such as amino sugars and the like may also be present. It will be understood that these hypothetical structures do not constitute any manner of limitation of the invention.

Chemical comparison of the four A38533 antibiotic complex factors described in U.S. Pat. No. 4,180,564 and the LL-BO2964α, β and γ antibiotic components of the present invention demonstrates their structural differences. For the four A38533 factors A1, A2, B and C, the elemental analyses reported for A1 and B, which are the major factors, indicate that they contain sulfur. The antibiotics of the invention, in contrast, have been analyzed for sulfur but do not contain it. Factor C of the A38533 complex exhibits a UV chromophore having a maximum absorption at 290 nm while the α, β and γ components of the invention show no similar UV absorption maximum. Finally, the retention time for high pressure liquid chromatography (HPLC) of the A38533 factors are significantly different from the HPLC retention times of the α, β and γ components of the invention when tested at the same time and under the same conditions. The details of the HPLC comparison are given in Table X, infra.

The antibiotics of the invention are formed by the cultivation, under controlled conditions, of *Streptomyces coeruleorubidus* subspecies *rubidus*. A representative strain of this microbe was isolated from a soil sample collected in Prescott, Ariz. and designated BO2964. An ultraviolet-induced mutant of this strain, designated BO2964 UV 14, has also been cultivated and produces antibiotics LL-BO2964α, LL-BO2964β, and LL-BO2964γ. They are both maintained in the culture collection of the Medical Research Division, American Cyanamid Company, Pearl River, N.Y. Viable cultures of both have been deposited with the Culture Collection Laboratory, Northern Utilization Research and Development Division, U.S. Department of Agriculture, Peoria, Ill., under accession numbers NRRL 12372 and NRRL 12373 (mutant).

The following general description characterizes the microorganisms *Streptomyces coeruleorubidus* subspecies *rubidus* as represented by the strain NRRL 12372. The UV mutant strain of *Streptomyces coeruleorubidus* subspecies *rubidus* as represented by NRRL 12373 has also been characterized and differences between the parent and mutant strains are pointed out where appropriate.

Observations of the cultural, physiological and morphological features of the microorganism were made in accordance with the methods detailed by Shirling, E. B. and D. Gottlieb, *Internat. J. of Syst. Bacteriol.* 16: 313-340 (1966). Media used were selected from those recommended by Pridham, et. al., *Antibiotics Annual*, 947-953 (1956/57) and Gordon, R. E., "The Taxonomy of Soil Bacteria", in *The Ecology of Soil Bacteria*, [T. G. R. Gray and D. Parkinson, eds.], pp. 293-321, Liverpool University Press, Liverpool, England (1967), for the taxonomic study of actinomycetes and soil bacteria, respectively. Chemical composition of the cell walls was determined using the method of Lechevalier, et. al., *Adv. Appl. Microbiol.* 14: 47-52 (1971) as modified by Stancek, J. L. and G. D. Roberts, *Appl. Microbiol.* 28: 226-234 (1974). Details are tabulated in the Examples section and overall descriptions of the cultures are summarized immediately hereafter. Underscored descriptive colors are taken from Kelly, K. L. and D. B. Judd, "Color. Universal Language and Dictionary of Names", U.S. Nat. Bur. Stand. Spec. Publ. 440, Washington, D.C. (1976) and the accompanying Inter-Society Color Council, National Bureau of Standards Centroid Color Charts.

Micromorphology

Spores are formed in long spiral chains (spira) on aerial sporophores. The spores are ovoid (0.7-1.0 micron×0.9-1.0 micron) and the surface of the mature spores is ornamented with spines approximately 100 nanometers in length. Both strains appear similar when observed by scanning electron microscopy.

Cell Wall Composition

Whole-Cell hydrolysates of these cultures contain the L,L-isomer of diaminopimelic acid, placing them in the Type I cell wall group classified according to the method of Lechevalier, cited above, as modified by Stancek, cited above. This is typical of all Streptomyces species.

Amount of Growth

Good growth is observed on most media; moderate growth is observed on inorganic salts-starch agar and nutrient agar.

Aerial Mycelium and Spore Color

Aerial mycelium is white; spore masses are blue shades ranging from 185. pale blue to 190. light bluish gray. Sporulation is moderate to heavy, dependent on the medium. The mutant strain generally exhibits less sporulation than the parent strain on most media.

Soluble Pigments

Soluble pigments are absent when the strains are grown on nutrient media including Benedict's agar, glycerol-aspargine agar and oatmeal agar. Reddish to reddish-brown pigments are produced by both strains when grown on the following nutrient media: asparagine-dextrose agar, Czapeck's agar, yeast extract-malt extract agar, Bennett's agar, Hickey-Tresner agar, inorganic salts starch agar, tomato paste-oatmeal agar. Pigment production is somewhat suppressed in the mutant strain.

Reverse Color

The reverse color produced by the strains grown on the nutrient media producing soluble pigment are pinkish-yellow to reddish-brown shades.

Physiological Reactions

The cultures display the following physiological reactions: nitrates reduced to nitrites; partial liquefaction of gelatin in 14 days; melanoid pigments produced on both peptone-yeast extract agar and tyrosine medium; hydrolysis of adenine, hypoxanthine and tyrosine, but not guanine and xanthine in 7 days. Carbohydrate utilization as per the method of Pridham, T. G. and D. Gottlieb, *J. Bacteriol.* 56: 107–114 (1948): good utilization of galactose, glucose, maltose, mannose, melibiose and xylose; moderate utilization of adonitol, arabinose, fructose, inositol, lactose, mannitol, raffinose, rhamnose, ribose and trehalose; poor utilization of sucrose; no utilization of glycerol or melezitose. The mutant strain exhibits moderate utilization of sucrose but poor utilization of melibiose. Both the parent and mutant strains tolerate 7% but not 10% sodium chloride.

A culture of the parent strain has been compared with Streptomyces reference cultures which have similar characteristics including blue spores, chromogenicity, and spiral spore chains with spiny spores. Of the four characteristic observed, which include spore color, soluble pigment, reverse color and amount of growth, no reference Streptomyces reference culture exhibited the same four characteristics as the *S. coeruleorubidus rubidus* of the invention. These comparisons are presented in detail in the Examples section.

Characterization of the microbial cultures of the invention as *S. coeruleorubidus rubidus* has been made because they most closely resemble the reference strain *Streptomyces coeruleorubidus*. The vegetative mycelia of the cultures on most media tend to have yellowish-pink shades and the cultures produce red soluble pigments on defined media. Moreover, the physiological reactions of the cultures also closely resemble those of the reference strain, although the reference strain does not reduce nitrates. The cultures of the invention are therefore assigned to the taxon *Streptomyces coeruleorubidus*, but because their production of red soluble pigments is far more prolific than the reference strain, they have been named as a new subspecies, namely *Streptomyces coeruleorubidus* subspecies *rubidus*.

It will be understood that for the purposes of the present invention, the production of the new antibiotics, LL-BO2964α, β, and γ, is not limited to the *S. coeruleorubidus rubidus* organism described in the foregoing passage or to microbes fitting the foregoing morphological, physiological growth characteristics. Use of these organisms is given for illustrative purposes only and production by any microbial means or combination of microbial and synthetic means is applicable to the invention. In fact, it is desired and intended to include the use of natural (spontaneous) mutants of this organism as well as induced and genetically engineered mutants produced from this organism by various means such as exposure to X-ray irradiation, ultraviolet irradiation, nitrogen mustard, actinophages, gene manipulation, recombinant DNA techniques and the like.

The antibiotics of the invention are active in vitro against gram positive and gram negative bacteria as shown by the minimal inhibitory concentrations of the antibiotics (MIC values) in mcg./ml. summarized in Table IV. The MIC's were determined by standard agar dilution procedures knwon to those skilled in the art. The MIC observations were made after incubation for 18 hours at 35° C. on Mueller-Hinton agar.

TABLE IV

IN VITRO ANTIBACTERIAL ACTIVITY OF THE ANTIBIOTICS OF THE INVENTION

| | | Minimal Inhibitory Concentration (mcg/ml) (e) | | |
|---|---|---|---|---|
| Organism | Cell Type (a) | LL-BO2964 Mixture of α, β and γ (b) | LL-BO2964 Mixture of α and β (c) | LL-BO2964γ (d) |
| *Pseudomonas aeruginosa* | SSC-78-13 | — | 64 | 64 | 64 |
| *Pseudomonas aeruginosa* | Strain 1 | | 16 | 16 | 16 |
| *Pseudomonas aeruginosa* | Strain 2 | | 16 | 16 | 16 |
| *Pseudomonas aeruginosa* | Strain 3 | | 16 | 16 | 16 |
| *Pseudomonas aeruginosa* | Strain 4 | | >1024 | >1024 | 1024 |
| *Klebsiella pneumoniae* | AD | — | 128 | 256 | 64 |
| Entercoccus | OSU-75-1 | + | >1024 | 1024 | 256 |
| | SM-77-15 | | >1024 | 512 | 256 |
| *Micrococcus lutea* | PCI 1001 | + | 256 | 256 | 256 |
| *Serratia marcescens* | TUL-78-15 | — | >1024 | >1024 | >1024 |
| Salmonella Sp. | SSC-79-57 | — | >1024 | >1024 | >1024 |
| *Escherichia coli* | #331 | — | >1024 | >1024 | >1024 |

TABLE IV-continued

IN VITRO ANTIBACTERIAL ACTIVITY OF THE
ANTIBIOTICS OF THE INVENTION

| Organism | Cell Type (a) | Minimal Inhibitory Concentration (mcg/ml) (e) | | |
|---|---|---|---|---|
| | | LL-BO2964 Mixture of $\alpha$, $\beta$ and $\gamma$ (b) | LL-BO2964 Mixture of $\alpha$ and $\beta$ (c) | LL-BO2964$\gamma$ (d) |
| *Enterobacter aerogenes* STFD-79-14 | − | >1024 | >1024 | >1024 |

(a) Cell type: gram positive is designated + and gram negative is designated −.
(b) This LL-BO2964 mixture of $\alpha$, $\beta$ and $\gamma$ components contained 4% $\alpha$, 34% $\beta$ and 62% $\gamma$ according to high pressure liquid chromatographic analysis.
(c) This LL-BO2964 mixture of $\alpha$ and $\beta$ components contained 40% $\alpha$ and 60% $\beta$ according to high pressure liquid chromatographic analysis.
(d) The LL-BO2964$\gamma$ used was substantially pure and contained about 90% $\gamma$ component, 0% $\alpha$ component and about 10% unidentified impurities according to high pressure liquid chromatographic analysis.
(e) The MIC value of >1024 means the MIC value is above the highest concentration of antibiotics tested (1024 mcg/ml).

Antibiotics LL-BO2964$\alpha$, $\beta$ and $\gamma$ are also active in vivo against bacterial infections as demonstrated by their ability to control Pseudomonas, Klebsiella and Staphylococcus infections in mice. For example, the LL-BO2964 mixture of $\alpha$, $\beta$ and $\gamma$ components shows in vivo antibacterial activity against *Pseudomonas aeruginosa* 12-4-4 when administered to mice infected with this bacterium. In the test, the animals used were Charles River Lab CD-1 mice each weighing 20±2 g. The mice were injected intraperitoneally with 0.5 ml of *P. aeruginosa* [1.2×10⁵ CF units of microbe] contained in 5% mucin. LL-BO2964 antibiotic treatment doses were contained in 0.5 ml of 0.2% aqueous agar and were administered subcutaneously at 0, 2 and 4 hours after inoculation. Table V summarizes the in vivo activity of the LL-BO2964 antibiotic in this test. The results are recorded as number of mice alive over the total mice tested 7 days after infection.

TABLE V

IN VIVO ACTIVITY OF LL-BO2964(a)
AGAINST *P. aeruginosa*

| LL-BO2964(a) Dosage Amounts In mg/kg Per Dose | Alive/Total Mice Tested 7 Days After Infection |
|---|---|
| 1024 | 5/5 |
| 512 | 4/5 |
| Untreated controls | 0/10 |

(a)The LL-BO2964 antibiotic mixture used in this in vivo test contains 18% $\alpha$, 30% $\beta$ and 52% $\gamma$ components according to high pressure liquid chromatographic analysis.

Tests with Klebsiella and Staphylococcus showed approximately the same activity. In addition to their spectrum of antibacterial activity, the antibiotics of the invention are effective against *Mycobacterium smegmatis* and and *Mycobacterium tuberculosis*. In particular, antibiotic LL-BO2964 containing a mixture of the $\alpha$, $\beta$ and $\gamma$ components, antibiotic LL-BO2964 containing the $\alpha$ and $\beta$ components, and antibiotic LL-BO2964$\gamma$ were tested for bactericidal activity against *Mycobacterium smegmatis* ATCC 607 in Sauton's medium modified with 0.1% polysorbate 80. The test was conducted according to the procedure of A. L. Barry and L. D. Sabath, "Manual of Clinical Microbiology", 2nd Edition, p. 431 (1974). The results are summarized in Table VI.

TABLE VI

ACTIVITY OF THE ANTIBIOTICS AGAINST *M. SMEGMATIS*

| Concentration of antibiotic tested in mcg/ml | Colony Forming Units/ml. After 20 Hours Incubation at 37° C. (c) | | |
|---|---|---|---|
| | LL-BO2964 (a) $\alpha$, $\beta$ and $\gamma$ components | LL-BO2964 (b) $\alpha$ and $\beta$ components | LL-BO2964$\gamma$ |
| 256 | $1.2 \times 10^3$ | $8.2 \times 10^3$ | $4.1 \times 10^3$ |
| 128 | $1.0 \times 10^3$ | $2.3 \times 10^3$ | $1.4 \times 10^3$ |
| 64 | $9.7 \times 10^5$ | $5.6 \times 10^4$ | $3.2 \times 10^6$ |

(a) This LL-BO2964 mixture contained 4% $\alpha$, 34% $\beta$ and 62% $\gamma$.
(b) This LL-BO2964 mixture contained 40% $\alpha$ and 60% $\beta$.
(c) Inoculum: $8 \times 10^6$ colony forming units/ml.

Using the following procedure, antibiotic LL-BO2964 containing $\alpha$ and $\gamma$ were tested for activity against *Mycobacterium tuberculosis* H37Rv. Test groups of five Charles River CF-1 female albino mice, each weighing about 18–20 g., were intravenously injected with 0.2 ml. of a buffered saline suspension containing 0.3 mg. (wet weight) of cells gathered from a 14-day old culture of *Mycobacterium tuberculosis* H37Rv, grown on Sauton's agar. The antibiotics were daily administered by gavage (o.t.), subcutaneous (s.c.) or intraperitoneal (i.p.) routes to the test groups of mice and each test group received a different dose. The antibiotic formulations for administration constituted suspensions in 0.2% aqueous agar or physiological saline with the concentrations of the antibiotics adjusted so that the required daily dose volume was 0.5 ml. The course of treatment started with the day of infection and ended 14 days later. Antibiotic activity was measured by the survival ratios of mice at 30 days postinfection. Deaths were recorded daily. Antibiotics protecting at least two out of five mice for 30 days were considered to be active. The positive and null control groups for the tests conducted on each antibiotic constituted ten to twenty infected, untreated mice (IUC) and ten unifected, untreated mice (UUC). Only one of the 70 infected mice used as the positive controls (IUC) for the total number of tests survived the 30 day test period. The results of the tests are summarized in Tables VII through VIII. Tests using differing routes of administration of LL-BO2964 were conducted as separate studies and are noted as runs 1 and 2 in Table VII.

TABLE VII

ANTITUBERCULER ACTIVITY OF LL-BO2964
(α, β and γ components)*

| Dose of LL-BO2964 (α, β, γ)* in mg./kg./day | 30-Day Postinfection Survival Ratios | |
|---|---|---|
| | s.c. | o.t. |
| *Run 1* | | |
| 400 | 5/5 | — |
| 200 | — | 4/5 |
| 100 | 2/5 | 3/5, 5/5+ |
| 50 | — | 3/5 |
| Infected, untreated controls (IUC) | 0/10 | 1/20 |
| | i.p. | o.t. |
| *Run 2* | | |
| 400 | 2/5 | — |
| 100 | 3/5 | 3/5 |
| IUC** | | 0/20 |

*The weight percent of components in this LL-BO2964 mixture was 4% α, 34% β and 62% γ.
+In a separate study, a second group was tested O.T. at this dosage and had the indicated survival ratio.
**One IUC group of 20 mice was used for Run 2.

TABLE VIII

ANTITUBERCULAR ACTIVITY OF LL BO2964β and LL-BO2964γ

| Gavage (o.t.) dose of β or γ in mg./kg./day | 30-Day Postinfection Survival Ratios | |
|---|---|---|
| | LL-BO2964β | LL-BO2964γ |
| 400 | 4/5 | 3/5 |
| IUC | 0/20 | |

Cultivation or fermentation of *Streptomyces coeruleorubidus* subspecies *rubidus* NRRL 12372 or NRRL 12373 may be carried out in a wide variety of liquid media. Media which will be useful include those containing an assimilable source of carbon such as starch, sugar, molasses, and the like; an assimilable source of nitrogen such as protein, protein hydrolysate, polypeptides, amino acids, corn steep liquor and the like; and inorganic anions and cations known to be necessary for microbial growth, such as potassium, sodium, ammonium, calcium, sulfate, carbonate, phosphate, chloride and the like. Trace elements which are also known to be necessary for microbial growth, such as boron, molybdenum, copper and the like will be supplied as impurities of other constituents of the media. Aeration in tanks, bottles and flasks can be provided by forcing sterile air through the fermenting medium or onto its surface. Further agitation in tanks can be provided by mechanical means. Anti-foaming agents such as lard oil or silicone defoamer may be added where appropriate. Specific methods and procedures for fermentation are provided in the Examples section.

Generally, the antibiotics LL-BO2964α, β and γ can be isolated and purified by methods known to those skilled in the art. These include filtration through filter aids such as diatomaceous earth and the like, chromatography on molecular gel or ion exchange columsn, high pressure liquid chromatography, electrophoresis, dialysis, electrodialysis and partition between organic and aqueous solvents. In a typical procedure, the LL-BO2964α, β and γ components can be isolated and grossly separated from the fermentation broth by absorption of the fermentation filtrate on a column of macroreticular resin and elution of the column with aqueous alcohol mixtures. The LL-BO2964 component mixture can be partitioned between 1-butanol and water and the antibiotic components, which will be contained in the 1-butanol phase, can be concentrated by vacuum removal of the solvent and further purified by chromatography on a cation exchange molecular gel such as CM-SEPHADEX ® [a modified dextrin cation exchange gel manufactured by Pharmacia, Inc., Piscataway, N.J.]. The substantial separation of the α, β and γ antibiotic components can be achieved by molecular gel filtration chromatography or partition chromatography on such materials as cross-linked, swelled dextrin gel, microcrystalline cellulose, or polyacetylamide gels.

Substantial separation of the individual α, β and γ antibiotic components as well as identification of the components separated according to the foregoing procedures can be respectively and conveniently accomplished by preparative or analytical high pressure liquid chromatography (HPLC). Generally, those skilled in the art will be able to ascertain column and eluant types to produce satisfactory results. Colums such as gels, macroreticular resins and polyacrylamide and aqueous solutions of polar organic solvents, in particular, will be useful. The preferred HPLC columns for the separation and identification of the α, β and γ antibiotic components are a column of Zorbax ODS ® [an absorptive bead material manufactured by Dupont, Inc., Wilmington, Del.]; or Ultrasphere-Octyl ® [a coating silica manufactured by Altex, Inc., California]. Typical HPLC conditions employed with these columns are a solvent system containing 0.1 M ammonium acetate at pH 5.0 and acetonitrile at a ratio of 85/15 parts by volume; a flow rate of 1.2 ml per minute; and a UV variable detector at 254 nm and 275 nm wavelenghts. Other conditions will be readily determinable by those skilled in the art.

The antibiotic component retention times and volumes on a Zorbax ODS ® column under the foregoing typical conditions, which were produced by introduction of 2.5 micrograms α, 5 micrograms β and 5 micrograms γ, are given in Table IX.

TABLE IX

HPLC OF ANTIBIOTICS ON ZORBAX ODS ®

| Component | Retention Time (minutes) | Retention Volume (ml.) |
|---|---|---|
| α | 3.1 | 3.7 |
| β | 5.5 | 6.6 |
| γ | 7.7 | 9.2 |

A comparative study of the HPLC curves produced by the antibiotic components of the invention and the factors of the A38533 complex described in U.S. Pat. No. 4,180,564 was conducted under the same conditions except that a column of Ultrasphere-Octyl ® was used. The results of this study were recorded as retention volumes (RV) in ml. and are presented in Table X.

TABLE X

COMPARATIVE STUDY ON ULTRASPHERE-OCTYL ®

| A38533 Factor | RV (ml) | LL-BO2964 component | RV (ml) |
|---|---|---|---|
| A1 | 7.2 | α | 5.1 |
| A2 | 19.2 | β | 9.0 |
| B | 34.8 | γ | 13.8 |
| C | 56.4 | | |

The following Examples further describe several embodiments of the invention including morphological, physiological and growth characteristics of cultures of *S. coeruleorubidus rubidus* on several types of media, methods for the fermentation of this microbe and methods for the production of the α, β and γ antibiotic components. These examples are not meant to be limitations of the invention, however.

EXAMPLE 1

Culture Characterization and Fermentation of Streptomyces coeruleorubidus rubidus A. Culture Characterization Observations of the cultural, physiological and morphological features of *S. coeruleorubidus rubidus* were made in accordance with the methods detailed by E. G. Shirling, and D. Gottlieb, cited supra. The culture media used were selected from those recommended by Pridham and P. E. Gordon for the taxonomic study of actinomycetes and soil bacteria, cited supra. Chemical composition of the cell walls was determined using the method of Lechevalier, as modified by J. L. Stancek, cited supra. Underscored descriptive colors are taken from K. L. Kelly and D. B. Judd, "Color. Universal Language and Dictionary of Names", cited supra, and the accompanying Inter-Society Color Council, National Bureau of Standards Centroid Color Charts.

Tables XI, XII and XIII, which follow, respectively summarize the observed cultural characteristics of the microorganism of the invention in standard media, miscellaneous physiological reactions and carbon source utilization. The cultural, physiological and utilization differences exhibited by mutant strain NRRL 12373 are noted in the overall description of these characteristics given in the foregoing general discussion of the microbes of the invention.

TABLE XI

CULTURAL CHARACTERISTICS OF *Streptomyces coeruleorubidus* subsp. *rubidus* NRRL 12372 and NRRL 12373*
Incubation period: 14 days at 28° C.

| MEDIUM | AMOUNT OF GROWTH | AERIAL MYCELIUM and/or SPORES | SOLUBLE PIGMENT | REVERSE COLOR |
|---|---|---|---|---|
| Asparagine-Dextrose | good | white aerial mycelia becoming 190. light bluish gray in sporulating areas. Sporulation heavy. | reddish | 30. dark yellowish pink |
| Bennett's Agar | good | white aerial mycelia becoming 190. light bluish gray in sporulating areas. Sporulation heavy. | reddish-brown | 30. dark yellowish pink |
| Benedict's Agar | good | trace of white aerial mycelia; no sporulation | none | 73. pale orange yellow |
| Czapek's Agar | good | white aerial mycelia; no sporulation. | reddish | 29. moderate yellowish pink |
| Glycerol-Asparagine | good | white aerial mycelia becoming 190. light bluish gray to 185. pale blue in sporulation areas. Sporulation heavy. | none | 29. moderate yellowish pink |
| Hickey-Tresner Agar | good | white aerial mycelia becoming 190. light bluish gray in sporulated areas. Sporulation heavy. | reddish-brown | 47. dark grayish reddish brown |
| Inorganic Salts Starch Agar | moderate | sparse white aerial mycelia; no sporulation. | faint reddish | 31. pale yellowish pink |
| Nutrient Agar | moderate | white aerial mycelia; no sporulation. | brownish | 33. brownish pink |
| Oatmeal Agar | good | white to yellowish aerial mycelia becoming 190. light bluish gray to 185. pale blue in sporulated areas. sporulation heavy | none | colorless |
| Tomato-Paste-Oatmeal Agar | good | white to yellowish aerial mycelia becoming 190. light bluish gray; sporulation heavy | reddish-brown | 47. dark grayish reddish brown |
| Yeast Extract | good | white aerial mycelia becoming 190. light bluish gray in sporulated areas. sporulation heavy | reddish-brown | 47. dark grayish reddish brown |

*NRRL 12373 differences as noted in general discussion of the microbes.

TABLE XII

MISCELLANEOUS PHYSIOLOGICAL REACTIONS OF
*Streptomyces coeruleorubidus* subsp. *rubidus*
NRRL 12373 and NRRL 12373*

| MEDIUM | INCUBATION PERIOD | AMOUNT OF GROWTH | PHYSIOLOGICAL REACTION |
|---|---|---|---|
| Peptone-Iron Agar | 72 hours | good | moderate amount of melanoid pigment produced |
| Tyrosine Medium | 3 days | good | slight blackening |
| Litmus Milk | 7 days | good | slight blackening |
|  | 7 days | good | slight proteolysis |
|  | 14 days | good | neutral pH; moderate peptonization |
| Nutrient Gelatin | 7 days | good | slight proteolysis |
|  | 14 days | good | moderate proteolysis |
| Organic Nitrate Broth | 7 days | good | nitrates reduced to nitrites |
|  | 14 days | good | nitrates reduced to nitrites |
| NaCl Tolerance Agar | 14 days |  | tolerates 7% NaCl but not 10% NaCl |
| Adenine Agar | 7 days | good | hydrolysis |
| Guanine Agar | 7 days | good | hydrolysis |
| Hypoxanthine Agar | 7 days | good | hydrolysis; melanoid pigment production |
| Tyrosine Agar | 7 days | good | hydrolysis; melanoid pigment production |
| Xanthine | 7 days | good | no hydrolysis |

*NRRL 12373 differences as noted in the general discussion of the microbes.

TABLE XIII

CARBON SOURCE UTILIZATION PATTERN OF
*STREPTOMYCES COERULEORUBIDUS* SUBSPECIES
*RUBIDUS* NRRL 12373 and NRRL 12373*
Incubation period: 14 days at 28° C.

| CARBON SOURCE | UTILIZATION+ |
|---|---|
| Adonitol | 2 |
| l-Arabinose | 2 |
| Fructose | 2 |
| d-Galactose | 3 |
| d-Glucose | 3 |
| Glycerol | 0 |
| i-Inositol | 2 |
| Lactose | 2 |
| Maltose | 3 |
| d-Mannitol | 2 |
| d-Mannose | 3 |
| d-Melezitose | 0 |
| d-Melibiose | 3 |
| d-Raffinose | 2 |
| l-Rhamnose | 2 |
| d-Ribose | 2 |
| Sucrose | 1 |
| d-Trehalose | 2 |
| d-Xylose | 3 |
| Negative Control | 0 |

*NRRL 12373 differences as noted in the general discussion of the microbe.
+3 = Good utilization
2 = fair utilization
1 = Poor utilization
0 = No utilization Comparative studies of the morphological and growth characteristics of the parent strain NRRL 12372 and several reference strains of Streptomyces microorganisms were conducted by culturing slants of the strains on asparagine-dextrose agar at about 38° C. for about 14 days according to standard culture production methods. The comparative spore color, soluble pigment, reverse color and growth characteristics of these strains observed during these studies are summarized in Table XIV.

TABLE XIV

COMPARATIVE OBSERVATIONS OF STREPTOMYCES CULTURES GROWN ON ASPARAGINE-DEXTROSE AGAR

| CULTURE | SPORE COLOR | SOLUBLE PIGMENT | REVERSE COLOR | GROWTH |
|---|---|---|---|---|
| S. caelestis AZ801 (NRRL 2418) | pale blue | yellow | light yellow | good |
| S. chartreusis AE4 (NRRL B-2287) | light bluish-gray to pale blue | pale yellow | light yellow | good |
| S. chartreusis BE821 (NRRL B-2199) | light greenish-gray | none | light yellowish-brown | good |
| S. coeruleofuscus BB102 (Gause 5051/56) | light bluish-gray | none | light to moderate yellow | good |
| S. coeruleorubidus BB103 (ATCC 13740) | very pale blue | reddish | moderate yellowish-pink | moderate |
| S. coerulescens BB104 (Gause 4562) | light bluish-gray | none | pale yellow | moderate |
| S. coeruleorubidus rubidus (NRRL 12372) | very pale blue | reddish | dark yellowish-pink | good |

B. Inoculum Preparation of *S. coeruleorubidus rubidus*

An inoculum medium having the following formulation was prepared:

Cornstarch: 24 g.
Glucose: 5 g.
Yeast extract: 5 g.
Bacto ®-tryptone[1]: 5 g.
Beef extract: 3 g.
Calcium carbonate: 4 g.
Water to: 1000 ml.

[1][A peptone, registered trademark of Difco Laboratories, Detroit, Mich.]

Washed or scraped spores from an agar slant of *Streptomyces coeruleorubidus* subspecies *rubidus* NRRL 12372 were used to inoculate 100 ml. of the foregoing sterile medium contained in a 500 ml flask. Two such flasks were placed on a rotary shaker and agitated at 180 r.p.m. and 28° C. for 48 hours. The resulting flask inoculum was then transferred to a 12 liter bottle containing the same sterile medium and incubated at 28° C. for 48 hours with sterile aeration. The resulting bottle inoculum was used to inoculate a tank containing 300 liters of the same sterile medium. The inoculated tank medium was incubated by agitating and aerating with sterile air at 28° C. for 24 hours to produce a tank inoculum. The inoculation conditions for flasks, bottle and tank fermentation may also vary from 24°–35° C. and from 20–56 hours. Aeration may be surface or in depth delivery of essential gases, typically sterile air through fritted glass, a bubble or other similar device. A medium of cornstarch, maltose and soy peptone, sterilized and adjusted to pH 7 with phosphate or similar buffer may also be used. Silicone antifoaming agent or other similar agent may be added to control fermentation frothing.

C. Bulk Fermentation

A fermentation medium of the following formula which was suitable for bulk production of *S. coeruleorubidus rubidus* was prepared.

Cornstarch: 10 g.
Maltose: 20 g.
Soy peptone: 10 g.
Water to: 1000 ml.

Fifteen hundred liters of this medium adjusted to pH 7 was sterilized at 120° C. for 60 minutes, and then inoculated with 150 liters of the tank *S. coeruleorubidus rubidus* inoculum described in section A. Bulk fermentation was then carried out at 28° C., using a silicone antifoam to control frothing. Aeration was supplied as 0.66 liters of sterile air per liter of microbe-medium mash per minute. The microbe-medium mash was agitated by impellers driven at 100 r.p.m. After fermenting for approximately 90 hours, the mash was harvested.

EXAMPLE 2

Preparation of the α, β and γ Antibiotic Components

A. Isolation of The Components

A fermentation is carried out as described in Example 1. The harvest mash (1450 l.) produced by the bulk fermentation of Example 1 was adjusted to pH 5.5 with 1.2 l. of concentrated hydrochloric acid, then combined with 43.5 kg. of diatomaceous earth and filtered through a filter press. The pad on the press was washed with water and the water wash was pooled with the filtrate. The pooled filtrate (1500 l.) was percolated through a 38 l. bed volume of cross-linked polystyrene macroreticular resin Amberlite ® XAD-2 [Rohm and Haas, Philadelphia, Pa.], at a flow rate of 1600–1900 ml. per minute. After percolation was completed, the resin was washed with 152 l. of demineralized water and then eluted with 200 l. of methanol:water (4:1). Ten 20 l. fractions were collected. Each fraction was checked for antibacterial activity by bioassay against *E. coli* or *P. aeruginosa*. Fractions 2–5 showed activity and were pooled and concentrated under reduced pressure to produce an antibiotic concentration in aqueous solution. This concentrate was extracted with an equal volume of 1-butanol and the 1-butanol phase separated and saved. The aqueous phase was then adjusted to pH 2.9–3.1 with 6N hydrochloric acid and extracted three times with equal volumes of 1-butanol. All butanol phases from both extractions were combined and concentrated under reduced pressure to a volume of about 15 liters. The resulting liquid concentrate was decanted and the remaining tarry residue saved. The concentrate was centrifuged to cause sedimentation and both the supernatant and sedimented product collected and saved. The sediment product was slurried with ethyl acetate and filtered. The filtered solid product was vacuum dried to yield 166 g. of yellow material. The tarry residue from the still was washed with 4 liters of a 1-butanol solution saturated with water. The saturated butanol washing was pooled with the supernatant from the centrifugation and concentrated under reduced pressure to about 3 liters which was cooled to cause precipitation. The resulting precipitate is collected by centrifugation, washed with ethyl acetate, filtered and vacuum dried to yield an additional 95 g. of solid product.

B. Purification of the α, β and γ Antibiotic Components

A chromatographic column (4.2×130 cm) was prepared with SP-Sephadex ® gel (Pharmacia Fine Chemicals, Piscataway, N.J.). A 13 g. portion of the isolated α, β and γ antibiotic component mixture of preceeding section A was added to 40 ml. of water, the pH adjusted to 7.8 using 1N sodium hydroxide and the mixture gently warmed over steam to cause dissolution. The solution was then absorbed onto the column of Sephadex ® gel and the column was developed with water. Fractions of 45 ml. were collected and each was checked for antibacterial activity by bioassay on large agar plates seeded with a strain of *Escherichia coli* and/or *Pseudomonas aeruginosa*. Fractions 24–89 were combined and freeze-dried to yield about 3.5 g. of the LL-BO2964 mixture of α, β and γ antibiotic components.

In a second, alternative purification precedure, a chromatographic column (4.2×130 cm.) was prepared with a gel of SP-Sephadex ®. A 12 g. portion of the isolated α, β and γ component mixture of section A was added to 40 ml. of water, the resulting mixture gently warmed and the pH adjusted to 7.5–8.0 with 5N sodium hydroxide. This solution was then absorbed onto the Sephadex ® gel column and the column washed with 25 ml. of water, then developed with 0.1M aqueous ammonium acetate. Fractions of 45 ml. were collected and each was checked for antibacterial activity by the bioassay given supra. Fractions 21–35 were combined, desalted using Amberlite ® XAD-2 resin and freeze-dried to yield about 7.7 g. of the LL-BO2964 mixture of α, β and γ antibiotic components.

In general, the individual fractions produced by these purification procedures will contain a mixture of α, β and γ antibiotic components wherein the proportional ratios of components will vary from fraction to fraction.

EXAMPLE 3

Separation of Antibiotic LL-BO2964γ and a Mixture of Antibiotics LL-BO2964α and β

A chromatographic column (5×90) was prepared with a polyacrylamide gel, Bio-Cel ® P-4 (50–100 mesh) [Bio Rad Laboratories, Richmond, Calif.]). A LL-BO2964 mixture of α, β and γ antibiotic components purified as described in Example 2, and weighing about 2.4 g. was added to 40 ml. of water, the mixture warmed and the pH adjusted to 7.7 with dilute ammonium hydroxide. The resulting solution was absorbed onto the Bio-Gel ® column, the column developed with water and fractions of 22 ml. collected. Aliquots of the column fractions were examined by thin layer chromatography on UV active polyamide plates. The chromatograms were developed with 2M ammonium acetate-methanol (7:3 v/v) and the zones were detected as yellow spots by spraying with a 1% aqueous solution of p-nitrobenzenediazonium tetrafluoroborate. The antibiotics appeared as yellow zones on the thin layer chromatogram. Two antibiotic components were evident; the first, LL-BO2964α, had an Rf value of 0.65 and the second was composed of a mixture of LL-BO2964α and LL-BO2964β as identified by analytical HPLC described supra.

Fractions 75–88, containing LL-BO2964γ were combined and freeze-dried to yield 675 mg. of the γ compound (portion H). Fractions 64–68, containing a mixture of LL-BO2964α and β were combined and freeze-dried to yield 771 mg. of a mixture of the α and β components (portion I). Fractions 69–74, containing all three components, α, β and γ, were combined and freeze-dried, to yield 287 mg. of a mixture of the α, β and γ components (portion J).

LL-BO2964γ isolated and separated according to this procedure had the following characteristics:

Microanalysis (percent): C, 52.87; H, 5.75; N, 15.10; O (direct), 21.19; S, 0.00.

Optical Rotation: $[\alpha]_D^{26} = -20\pm2°$ (C=0.5%, water).

LL-BO2964γ produced an infrared absorption spectrum (KBr pellet) as shown in FIG. 11; a U.V. spectrum in water exhibiting absorption maxima at 225 and 259 nm as shown in FIG. 12; $^1$HMR spectra relative to tetramethyl silane in δppm, taken as a solution in D$_6$ dimethyl sulfoxide, as shown in FIG. 13 and under the same conditions and with added deutero trifluoroacetic acid as shown in FIG. 14; and a carbon-13 NMR spectrum relative to tetramethyl silane in ppm, taken as a solution in D$_6$ dimethyl sulfoxide, as shown in FIG. 15. The significant carbon-13 NMR absorptions are tabularized in Table I.

EXAMPLE 4

Separation of Antibiotic LL-BO2964α

A chromatographic (5×90 cm) column was prepared with a gel of polyacrylamide gel Bio-Gel ® P-4 (50-100 mesh). A 1682 mg. portion of a mixture of α, β and γ antibiotic components similar to portion (J) of Example 3 was dissolved in 40 ml. of water and absorbed onto the Bio Gel ® column. The column was developed with water and 15 ml. fractions were collected. Fractions 73–77, which contained LL-BO2964 according to an HPLC analysis conducted as described supra, were combined and freeze-dried, to yield 430 mg. of the antibiotic LL-BO2964 having the following characteristics:

Microanalysis (percent): C, 50.89; H, 5.67; N, 14.44; S, 0.00

Optical Rotation: $[\alpha]_D^{25} = -10°$ (C—2.77%, water)

LL-BO2964α produced an infrared absorption spectrum (KBr pellet) as shown in FIG. 1; a U.V. spectrum in water exhibiting absorption maxima at 221 and 254 nm as shown in FIG. 2; $^1$HMR spectra relative to tetramethyl silane in ppm, taken as a solution in D$_6$ dimethyl sulfoxide, as shown in FIG. 3 and under the same conditions with added deutero trifluoro acetic acid as shown in FIG. 4; and a carbon-13 NMR spectrum relative to tetramethyl silane in δppm, taken as a solution in D$_6$ dimethyl sulfoxide, as shown in FIG. 5. The significant carbon-13 NMR absorptions are tabularized in Table I. This preparation is essentially homogeneous by analytical HPLC on Ultrasphere-Octyl ® gel with an aqueous ammonium acetate and acetonitrile solvent system.

EXAMPLE 5

Separation of Antibiotic LL-BO2964β

A 1182 mg. portion of a mixture of α and β components similar to portion (I) of Example 3 was chromatographed on Bio-Gel ® P-4 as described in Example 4. Fractions 55–59, containing antibiotic LL-BO2964β according to an HPLC analysis conducted as described supra, were combined and freeze-dried to yield 110 mg. of antibiotic LL-BO2964β, having the following characteristics:

Microanalysis (percent): C, 50.91; H, 5.79; N, 13.57; S, 0.00

Optical Rotation: $[\alpha]_D^{25} = -19\pm2°$ (C=0.5%, water)

LL-BO2964β produced an infrared absorption spectrum (KBr pellet) as shown in FIG. 6; a U.V. spectrum in water exhibiting absorption maxima at 220 and 256 nm as shown in FIG. 7; $^1$HMR spectra relative to tetramethyl silane in ppm, taken as a solution in D$_6$ dimethyl sulfoxide, as shown in FIG. 8 and under the same conditions with added deutero trifluoroacetic acid, as shown in FIG. 9; and a 13CNMR spectrum relative to tetramethyl silane in ppm, taken as a solution in D$_6$ dimethyl sulfoxide, as shown in FIG. 10. The significant $^{13}$CNMR absorptions are tabularized in Table I.

EXAMPLE 6

Analysis of the Amino Acid Esters Obtained by Acid Hydrolysis of the α, β and γ Antibiotic Components The individual α, β and γ antibiotics were separately hydrolyzed by dissolving each in 6N hydrochloric acid (1 mg antibiotic to 1 ml acid ratio) and heating in a sealed tube for 24 hours at 110° C. The amino acid residue recovered from the hydrolysis was washed several times with water while processing on a rotary evaporator which removed excess hydrochloric acid. The residue was then placed under high vacuum for 16 hours.

The procedure used to prepare the N-trifluoroacetyl-n-butyl ester derivatives of the amino acid residues was essentially that of Pandey, et. al., *J.A.C.S.* 99: 8469 (1977). This procedure was carried out on each of the foregoing antibiotic hydrolysates. A 6 mg. portion of the acid hydrolysate suspended in 1 ml. of 3N hydrochloric acid in 1-butanol was sealed in a hydrolysis tube and heated at 110° C. for 30 minutes. The reaction mixture was cooled and evaporated to dryness in vacuo. A 2 ml. portion of 1-butanoltanol was added to the residue and the mixture was reevaporated in vacuo. The residue was then heated with 1 ml. of dichloromethane and 0.5 ml. of trifluorooacetic anhydride at 150° C. for 5 minutes in a sealed hydrolysis tube. The mixture was cooled, evaporated under a stream of nitrogen and the residue redissolved in 1 ml. of dichloromethane and errevaporated. The residue was taken up in 0.3 ml. of dichloromethane for analysis.

The gas chromatographic/mass spectrum analysis was performed under the following conditions: the column used was 3% OV-17 on GAS CHROM ®Q (100-200 mesh) (6 feet glass); the detector temperature was 300° C.; the injector temperature was 250° C.; helium was used as a carrier gas with a flow rate of 30 ml/minute; and the column temperature was programmed to increase from 80° to 300° C. at 15° C./minute and then to hold at 300° C. for 10 minutes.

As each ester fraction eluted from the gas chromatograph, an aliquot was automatically shunted into a mass spectrumeter which permitted determination of the molecular weight of the ester composing that fraction as well as the fragmentation pattern in the ester. In this manner, the molecular weights and identities of each of the esters of the amino acids present in each antibiotic hydrolysate were determined. Accordingly, the N-trifluoroacetyl-n-butyl esters of amino acids contained in the polypeptide chain of each antibiotic, LL-BO2964α, β and γ include the following:

β-Alanine Derivative: $CF_3CONHCH_2CH_2COOC_4H_9$
Alanine Derivative: $CF_3CONHCH(CH_3)COOC_4H_9$
Glycine Derivative: $CF_3CONHCH_3COOC_4H_9$
m-Tyrosine Derivative: $CF_3COOC_6H_4CH_2CH(NHCOCF_3)COOC_4H_9$
2-Amino-3-(methylamino) butyric acid Derivative: $CH_3N(COCF_3)CH(CH_3)CH(NHCOCF_3)COOC_4H_9$ In addition, three hydantoins formed from (i) alanine and m-tyrosine, (ii) alanine and phenylalanine and (iii) alanine and p-tyrosine were found in the acid hydrolysates of the α, β and γ components respectively. Uracil was also present in the three acid hydrolysates.

The antibiotic agents of the invention may be administered by conventional routes which would be apparent to those skilled in the art, and in appropriate dosage form such as sterile aqueous or alcoholic solution or suspension, liquid solution, suppository, capsule, tablet, troche, syrup, water, powder, elixir and the like. The agents may be given alone in the appropriate dosage form or may be combined with a suitable pharmaceutical carrier. Such carriers are well known in the art and include elixirs, excipients, starches, aliphatic alcohols, glycerols, glycols, sugar solids or liquids, polyvinyl pyrolidone, suspension agents, emulsifiers, inert pharmaceutically acceptable diluting powders and liquids, isotonic solutions, gums, gelatins, lubricants, sweetners, flavoring agents, preservatives, antioxidants and the like. The methods for preparing such combinations and dosage forms are well known in the art.

In general, the route of administration, dosage form and amount, and dosage rate will be dependent upon the patient's condition and upon the judgment and observation of his attending physician. An effective amount for the treatment of bacterial infection or tuberculosis can be determined by culturing the infectious organism by known techniques and determining the bacteriostatic or bacteriotoxic concentration of agent required to inhibit the growth or kill the organism. The physician will then use these data to determine the requisite parameters of administration to the patient. Typically, for antibacterial purposes, from about 30 to about 250 mg. of agent per kg. of patient body weight per day would be administered. For antitubercular treatment, from about 30 to 250 mg. of agent per kg. of patent body weight per day would be administered. Antitubercular treatment will generally require long periods of administration, typically six months to a year or more and may also be combined with other methods of therapy, such as use of isoniazid and the like.

We claim:

1. A biologically pure culture of a *Streptomyces coeruleorubidus* subspecies *rubidus* microorganism or mutant thereof which produces polypeptide antibiotics in recoverable quantity upon fermentation, wherein:

(a) the microorganism is of the Streptomyces genus and has ovoid spores ornamented with spines and formed in long spiral chains on aerial sporophores;
   (b) has a Type I cell wall group according to the Lechevalier method as modified by Stancek;
   (c) has white aerial mycelia;
   (d) physiologically reduces nitrates to nitrites, partially liquifies gelatin, hydrolyzes adenine, hypoxanthine, and tyrosine but not guanine and xanthine, utilizes d-galactose, d-glucose and maltose but not glycerol according to the Pridham and Gottlieb method; and
   (e) produces a reddish to reddish-brown pigment when grown on a nutrient medium selected from asparagine-dextrose agar, Czepeck's agar or yeast extractmalt extract agar.

2. A biologically pure culture of microorganisms selected from the group consisting of *Streptomyces coeruleorubidus* subspecies *rubidus* NRRL 12372, NRRL 12373 and mutants of both, said culture being capable of producing the antibiotic LL-BO2964α in recoverable quantity upon fermentation in an aqueous nutrient medium containing assimilable sources of carbon, nitrogen and inorganic anion and cation salts, wherein said antibiotic LL-BO2964α in substantially pure form:

(a) exhbits the following significant carbon-13 nuclear magnetic resonance absorptions (Abs) in parts per million in dimethylsulfoxide-d6 relative to the absorption of tetramethyl silane:

| Peak No. | Abs | Peak No. | Abs | Peak No. | Abs |
|---|---|---|---|---|---|
| 1 | 13.9 | 16 | 96.7 | 31 | 137.3 |
| 2 | 18.4 | 17 | 102.1 | 32 | |
| 3 | 27.3 | 18 | | 33 | 138.9 |
| 4 | | 19 | | 34 | 139.6 |
| 5 | 29.3 | 20 | 112.9 | 35 | 140.4 |
| 6 | 30.5 | 21 | 113.4 | 36 | 150.3 |
| 7 | 33.9 | 22 | 116.2 | 37 | 152.9 |
| 8 | 48.5 | 23 | | 38 | 156.9 |
| 9 | 49.5 | 24 | 119.3 | 39 | 157.3 |
| 10 | 50.4 | 25 | 119.9 | 40 | 162.7 |
| 11 | 55.0 | 26 | | 41 | 166.4 |
| 12 | 69.9 | 27 | 127.6 | 42 | 170.1 |
| 13 | 71.4 | 28 | 128.6 | 43 | 171.0 |
| 14 | 73.0 | 29 | 129.0 | 44 | |
| 15 | 91.5 | 30 | 135.8 | 45 | 173.1 |

(b) has an optical rotation $[\alpha]_D^{25}$ of $-10°$ (C being 2.77% water );
   (c) has an elemental analysis (percent) of about: C, 50.89; H, 5.67; N, 14.44; S, 0.00;
   (d) has a carbon-13 nuclear magnetic resonance spectrum in diemthyl sulfoxide-d6 substantially as shown in FIG. 5;
   (e) produces uracil, alanine, beta-alanine, glycine, m-tyrosine, 3-N-methylamino-2-aminobutyric acid and a hydantoin formed from alanine and tyrosine when hydrolyzed by acid; and
   (f) has an infrared absorption spectrum in KBr substantially as shown in FIG. 1, an ultraviolet spectrum in water substantially as shown in FIG. 2, a proton nuclear magnetic resonance spectrum in dimethyl sulfoxide-d6 substantially as shown in FIG. 3, and a proton nuclear magnetic resonance spectrum in dimethylsulfoxide-d6 with added deutero-trifluoroacetic acid substantially as shown in FIG. 4.

3. A biologically pure culture of microorganisms selected from the group consisting of *Streptomyces co-*

*eruleorubidus* subspecies *rubidus* NRRL 12372, NRRL 12373 and mutants of both, said culture being capable of producing the antibiotic LL-BO2964β in recoverable quantity upon fermentation in an aqueous nutrient medium containing assimilable sources of carbon, nitrogen and inorganic anion and cation salts, wherein said antibiotic LL-BO2964β in substantially pure form:

(a) exhibits the following significant carbon-13 nuclear magnetic resonance absorptions (Abs) in parts per million in dimethyl sulfoxide-d6 relative to the absorption of tetramethyl silane:

| Peak No. | Abs | Peak No. | Abs | Peak No. | Abs |
|---|---|---|---|---|---|
| 1 | 13.9 | 16 | 96.7 | 31 | |
| 2 | 18.3 | 17 | 102.1 | 32 | 138.4 |
| 3 | 27.3 | 18 | | 33 | 138.9 |
| 4 | | 19 | | 34 | |
| 5 | 29.3 | 20 | 113.4 | 35 | 140.4 |
| 6 | 30.4 | 21 | | 36 | 150.3 |
| 7 | 33.9 | 22 | 115.7 | 37 | 152.9 |
| 8 | 48.9 | 23 | | 38 | 156.9 |
| 9 | 49.6 | 24 | | 39 | 147.3 |
| 10 | 50.4 | 25 | 119.4 | 40 | 162.7 |
| 11 | 54.9 | 26 | 125.7 | 41 | 166.4 |
| 12 | 69.4 | 27 | 127.7 | 42 | 169.9 |
| 13 | 71.3 | 28 | 129.3 | 43 | 171.0 |
| 14 | | 29 | | 44 | |
| 15 | 91.4 | 30 | | 45 | 173.1 |

(b) has an optical rotation $[\alpha]_D^{25}$ of $-19\pm2°$ (C being 0.5%, water);
(c) has an elemental analysis (percent) of about: C, 50.91; H, 5.79; N, 13.57; S, 0.00;
(d) has a carbon-13 nuclear magnetic resonance spectrum in dimethyl sulfoxide-d6 substantially as shown in FIG. 10;
(e) produces uracil, alanine, beta-alanine, glycine, m-tyrosine, 3-N-methylamino-2-aminobutyric acid and a hydantoin formed from alanine and phenylalanine when hydrolyzed by acid; and
(f) has an infrared absorption spectrum in KBr substantially as shown in FIG. 6, and ultraviolet spectrum in water substantially as shown in FIG. 7, a proton nuclear magnetic spectrum in dimethyl sulfoxide-d6 substantially as shown in FIG. 8, and a proton nuclear magnetic resonance spectrum in dimethyl sulfoxide-d6 with added deutero-trifluoroacetic acid substantially as shown in FIG. 9.

4. A biologically pure culture microorganisms selected from the group consisting of *Streptomyces co-eruleoribidus* subspecies *rubidus* NRRL 12372, NRRL 12373 and mutants of both, said culture being capable of producing the antibiotic LL-BO2964γ in recoverable quantity upon fermentation in an aqueous nutrient medium containing assimilable sources of carbon, nitrogen and inorganic anion and cation salts, wherein said antibiotic LL-BO2964γ in substantially pure form:

(a) exhibits the following significant carbon-13 nuclear magnetic resonance absorptions (Abs) in parts per million in dimethyl sulfoxide-d6 relative to the absorption of tetramethyl silane:

| Peak No. | Abs | Peak No. | Abs | Peak No. | Abs |
|---|---|---|---|---|---|
| 1 | 13.9 | 16 | 96.7 | 31 | |
| 2 | 18.4 | 17 | 102.2 | 32 | |
| 3 | 27.4 | 18 | 110.3 | 33 | 138.9 |
| 4 | 28.1 | 19 | 111.0 | 34 | |
| 5 | 29.3 | 20 | 113.4 | 35 | 140.4 |
| 6 | 30.4 | 21 | | 36 | 150.3 |
| 7 | 33.9 | 22 | 115.7 | 37 | 153.0 |
| 8 | 48.7 | 23 | 118.0 | 38 | 156.9 |
| 9 | 49.4 | 24 | 118.5 | 39 | 157.4 |
| 10 | 50.4 | 25 | 120.5 | 40 | 162.7 |
| 11 | 54.2 | 26 | 123.4 | 41 | 166.4 |
| 12 | 69.5 | 27 | 127.6 | 42 | 170.0 |
| 13 | 71.4 | 28 | 129.0 | 43 | 171.1 |
| 14 | | 29 | | 44 | 171.9 |
| 15 | 91.5 | 30 | 135.8 | 45 | 173.1 |

(b) has an optical rotation $[\alpha]26$ of $-20\pm2°$ (C being 0.5%, water);
(c) has an elemental analysis (percent) of about: C, 52.87; H, 5.75; N, 15.10; S, 0.00;
(d) has a characteristic carbon-13 nuclear magnetic resonance spectrum in diemthyl sulfoxide-d6 substantially as shown in FIG. 15;
(e) produces uracil, alanine, beta-alanine, glycine, m-tyrosine, 3-N-methylamino-2-aminobutyric acid and a hydantoin formed from alanine and tyrosine when hydrolyzed by acid; and
(f) has an infrared absorption spectrum in KBr substantially as shown in FIG. 11, an ultraviolet spectrum in water substantially as shown in FIG. 12, a proton nuclear magnetic resonance spectrum in dimethyl sulfoxide-d6 substantially as shown in FIG. 13, and a proton nuclear magnetic resonance spectrum in dimethyl sulfoxide-d6 with added deutero-trifluoroacetic acid substantially as shown in FIG. 14.

* * * * *